(12) United States Patent
Ou et al.

(10) Patent No.: US 8,198,091 B2
(45) Date of Patent: Jun. 12, 2012

(54) METHOD FOR ASSAYING THE ANTIOXIDANT CAPACITY OF A SKIN CARE PRODUCT

(75) Inventors: Boxin Ou, Franklin, MA (US); Liliang Zhang, Mansfield, MA (US); Miwako Kondo, Taunton, MA (US); Hongping Ji, Jiangsu (CN); Yan Kou, Jiangsu (CN)

(73) Assignee: Brunswick Laboratories, LLC, Norton, MA (US)

( * ) Notice: Subject to any disclaimer, the term of this patent is extended or adjusted under 35 U.S.C. 154(b) by 498 days.

(21) Appl. No.: 12/317,500

(22) Filed: Dec. 24, 2008

(65) Prior Publication Data
US 2010/0159613 A1 Jun. 24, 2010

(51) Int. Cl.
G01N 33/15 (2006.01)
G01N 33/02 (2006.01)
G01N 33/03 (2006.01)
G01N 33/26 (2006.01)

(52) U.S. Cl. ......... 436/60; 436/20; 436/22; 436/23; 436/24; 436/164; 436/166; 436/172; 436/179

(58) Field of Classification Search ......... 436/20, 436/22–24, 60, 164, 166, 172, 179
See application file for complete search history.

(56) References Cited

U.S. PATENT DOCUMENTS

| | | | |
|---|---|---|---|
| 7,132,296 B2 | 11/2006 | Ou et al. | |
| 2003/0162297 A1* | 8/2003 | Ou et al. | 436/62 |
| 2003/0207818 A1* | 11/2003 | Jia et al. | 514/27 |
| 2004/0109905 A1* | 6/2004 | Bagchi | 424/732 |
| 2004/0259187 A1* | 12/2004 | Aldini et al. | 435/25 |
| 2005/0042354 A1* | 2/2005 | Morimura et al. | 426/601 |
| 2005/0087452 A1* | 4/2005 | McAnalley et al. | 205/777.5 |
| 2005/0163880 A1* | 7/2005 | Pusateri et al. | 424/777 |
| 2005/0214413 A1* | 9/2005 | McAnalley et al. | 426/74 |
| 2006/0024390 A1* | 2/2006 | Schauss et al. | 424/727 |
| 2006/0045896 A1* | 3/2006 | Morariu | 424/401 |
| 2006/0216251 A1* | 9/2006 | Morariu | 424/59 |
| 2007/0167398 A1* | 7/2007 | Dillon et al. | 514/54 |
| 2007/0244175 A1* | 10/2007 | Beelman et al. | 514/401 |
| 2008/0206170 A1* | 8/2008 | Nivaggioli et al. | 424/59 |
| 2009/0258094 A1* | 10/2009 | Ono et al. | 424/744 |
| 2009/0285864 A1* | 11/2009 | Godin | 424/400 |
| 2010/0111878 A1* | 5/2010 | Maor et al. | 424/45 |
| 2010/0129465 A1* | 5/2010 | Blotsky et al. | 424/602 |
| 2010/0159041 A1* | 6/2010 | Ge et al. | 424/757 |

OTHER PUBLICATIONS

Marco, G. J., Journal of the American Oil Chemists' Society 1968, 45, 594-598.*

(Continued)

Primary Examiner — Arlen Soderquist
(74) Attorney, Agent, or Firm — Iandiorio Teska & Coleman, LLP

(57) ABSTRACT

A method for assaying the antioxidant capacity of a skin care product, the method including preparing an emulsion base, dissolving a sample of a skin care product into the emulsion base to form a homogeneous emulsion mixture, adding a detection probe to the homogeneous emulsion mixture, adding reactive oxygen species generator and/or reactive nitrogen species generator to the homogeneous emulsion mixture, measuring the fluorescence intensity change of the detection probe in the presence of the sample over time, in the presence of the standard over time, and in the presence of a blank over time, and calculating the initial rate of oxidation of the detection probe to determine the antioxidant capacity of the sample of the skin care product.

49 Claims, 14 Drawing Sheets

OTHER PUBLICATIONS

Aubry, J. M. et al, Journal of Organic Chemistry 1989, 54, 726-728.*
Uppu, R. M. et al, Methods in Enzymology 1996, 269, 285-295.*
Emmons, C. L. et al, Journal of Agricultural and Food Chemistry 1999, 47, 4894-4898.*
Chung, H.Y. et al, Journal of Agricultural and Food Chemistry 2001, 49, 3614-3621.*
Ou, B. et al, Journal of Agricultural and Food Chemistry 2001, 49, 4619-4626.*
Huang, D. et al, Journal of Agricultural and Food Chemistry 2002, 50, 1815-1821.*
Ou, B. et al, Journal of Agricultural and Food Chemistry 2002, 50, 2772-2777.*
Huang, D. et al, Journal of Agricultural and Food Chemistry 2002, 50, 4437-4444.*
Kurlich A. C. et al, Journal of Agricultural and Food Chemistry 2002, 50, 5053-5057.*
Pelle, E. et al, JOurnal of Cosmetic Science 2002, 53, 237-240.*
Prior, R. L. et al, Journal of Agricultural and Food Chemistry 2003, 51, 3273-3279.*
Akhter, S. et al, Nitric Oxide 2003, 8, 214-221.*
Davalos, A. et al, Journal of Agricultural and Food Chemistry 2004, 52, 48-54.*
Huang, D. et al, Journal of Agricultural and Food Chemistry 2005, 53, 1841-1856.*
Prior, R. L. et al, Journal of Agricultural and Food Chemistry 2005, 53, 4290-4302.*
Gorlach, A. et al, Methods in Enzymology 2007, 435, 421-446.*
Yuji, H. et al, Journal of Agricultural and Food Chemistry 2007, 55, 11052-11056.*
Chaiyasit, W. et al, Journal of Agricultural and Food Chemistry 2008, 56, 550-556.*
Qin, Y. et al, Cell Biology International 2008, 32, 224-228.*
Decker, E. A. et al, Journal of Agricultural and Food Chemistry 2005, 53, 4303-4310.*
Held, P., BioTek Application Note 2005, 9 pages.*
Gomes, A. et al, Journal of Biochemical and Biophysical Methods 2005, 65, 45-80.*
Laporta, O. et al, Journal of Agricultural and Food Chemistry 2007, 101, 1425-1437.*
Quantification of Polyphenols and Ergothioneine in Cultivated Mushrooms and Correlation to Total Antioxidant Capacity by Joy Dubost, Boxin Ou, and Robert B. Beelman, Food Chemistry 105 (2007) 727-735.
Quantification of Antioxidant Capacity in a Microemulsion System: Synergistic Effects of Chlorogenic Acid with α-Tocopherol by Wei Lin Sandra Sim, Ming Yong Han and Dejian Huang, J. Agric. Food Chem, 2009, 57, 3409-3414.

* cited by examiner

|   | 1 | 2 | 3 | 4 | 5 | 6 | 7 | 8 | 9 | 10 | 11 | 12 |
|---|---|---|---|---|---|---|---|---|---|----|----|----|
| A | Sample 1 1 | Sample 1 2 | Sample 1 4 | Sample 1 8 | Sample 1 16 | Sample 1 32 | Sample 6 32 | Sample 6 16 | Sample 6 8 | Sample 6 4 | Sample 6 2 | Sample 6 1 |
| B | Control 1 | Control 2 | Control 4 | Control 8 | Control 16 | Control 32 | Control 32 | Control 16 | Control 8 | Control 4 | Control 2 | Control 1 |
| C | Sample 2 1 | Sample 2 2 | Sample 2 4 | Sample 2 8 | Sample 2 16 | Sample 2 32 | Sample 7 32 | Sample 7 16 | Sample 7 8 | Sample 7 4 | Sample 7 2 | Sample 7 1 |
| D | Standard 1 | Standard 2 | Standard 4 | Standard 8 | Standard 16 | Standard 32 | Standard 32 | Standard 16 | Standard 8 | Standard 4 | Standard 2 | Standard 1 |
| E | Sample 3 1 | Sample 3 2 | Sample 3 4 | Sample 3 8 | Sample 3 16 | Sample 3 32 | Sample 8 32 | Sample 8 16 | Sample 8 8 | Sample 8 4 | Sample 8 2 | Sample 8 1 |
| F | Sample 4 1 | Sample 4 2 | Sample 4 4 | Sample 4 8 | Sample 4 16 | Sample 4 32 | Sample 9 32 | Sample 9 16 | Sample 9 8 | Sample 9 4 | Sample 9 2 | Sample 9 1 |
| G | Sample 5 1 | Sample 5 2 | Sample 5 4 | Sample 5 8 | Sample 5 16 | Sample 5 32 | Sample 10 32 | Sample 10 16 | Sample 10 8 | Sample 10 4 | Sample 10 2 | Sample 10 1 |
| H | Blank | Blank | Blank | Blank | Blank | Blank | Blank | Blank | Blank | Blank | Blank | Blank |

*FIG. 11*

|   | 1 | 2 | 3 | 4 | 5 | 6 | 7 | 8 | 9 | 10 | 11 | 12 |
|---|---|---|---|---|---|---|---|---|---|---|---|---|
| A | Sample 1<br>1 | Sample 1<br>2 | Sample 1<br>4 | Sample 1<br>8 | Sample 1<br>16 | Sample 1<br>32 | Sample 6<br>32 | Sample 6<br>16 | Sample 6<br>8 | Sample 6<br>4 | Sample 6<br>2 | Sample 6<br>1 |
| B | Standard<br>1 | Standard<br>2 | Standard<br>4 | Standard<br>8 | Standard<br>16 | Standard<br>32 | Standard<br>32 | Standard<br>16 | Standard<br>8 | Standard<br>4 | Standard<br>2 | Standard<br>1 |
| C | Control<br>1 | Control<br>2 | Control<br>4 | Control<br>8 | Control<br>16 | Control<br>32 | Control<br>32 | Control<br>16 | Control<br>8 | Control<br>4 | Control<br>2 | Control<br>1 |
| D | Sample 2<br>1 | Sample 2<br>2 | Sample 2<br>4 | Sample 2<br>8 | Sample 2<br>16 | Sample 2<br>32 | Sample 7<br>32 | Sample 7<br>16 | Sample 7<br>8 | Sample 7<br>4 | Sample 7<br>2 | Sample 7<br>1 |
| E | Sample 3<br>1 | Sample 3<br>2 | Sample 3<br>4 | Sample 3<br>8 | Sample 3<br>16 | Sample 3<br>32 | Sample 8<br>32 | Sample 8<br>16 | Sample 8<br>8 | Sample 8<br>4 | Sample 8<br>2 | Sample 8<br>1 |
| F | Sample 4<br>1 | Sample 4<br>2 | Sample 4<br>4 | Sample 4<br>8 | Sample 4<br>16 | Sample 4<br>32 | Sample 9<br>32 | Sample 9<br>16 | Sample 9<br>8 | Sample 9<br>4 | Sample 9<br>2 | Sample 9<br>1 |
| G | Sample 5<br>1 | Sample 5<br>2 | Sample 5<br>4 | Sample 5<br>8 | Sample 5<br>16 | Sample 5<br>32 | Sample 10<br>32 | Sample 10<br>16 | Sample 10<br>8 | Sample 10<br>4 | Sample 10<br>2 | Sample 10<br>1 |
| H | Blank | Blank | Blank | Blank | Blank | Blank | Blank | Blank | Blank | Blank | Blank | Blank |

*FIG. 12*

|   | 1 | 2 | 3 | 4 | 5 | 6 | 7 | 8 | 9 | 10 | 11 | 12 |
|---|---|---|---|---|---|---|---|---|---|----|----|----|
| A | Sample 1<br>1 | Sample 1<br>2 | Sample 1<br>4 | Sample 1<br>8 | Sample 1<br>16 | Sample 1<br>32 | Sample 6<br>32 | Sample 6<br>16 | Sample 6<br>8 | Sample 6<br>4 | Sample 6<br>2 | Sample 6<br>1 |
| B | Control<br>1 | Control<br>2 | Control<br>4 | Control<br>8 | Control<br>16 | Control<br>32 | Control<br>32 | Control<br>16 | Control<br>8 | Control<br>4 | Control<br>2 | Control<br>1 |
| C | Sample 2<br>1 | Sample 2<br>2 | Sample 2<br>4 | Sample 2<br>8 | Sample 2<br>16 | Sample 2<br>32 | Sample 7<br>32 | Sample 7<br>16 | Sample 7<br>8 | Sample 7<br>4 | Sample 7<br>2 | Sample 7<br>1 |
| D | Standard<br>1 | Standard<br>2 | Standard<br>4 | Standard<br>8 | Standard<br>16 | Standard<br>32 | Standard<br>32 | Standard<br>16 | Standard<br>8 | Standard<br>4 | Standard<br>2 | Standard<br>1 |
| E | Sample 3<br>1 | Sample 3<br>2 | Sample 3<br>4 | Sample 3<br>8 | Sample 3<br>16 | Sample 3<br>32 | Sample 8<br>32 | Sample 8<br>16 | Sample 8<br>8 | Sample 8<br>4 | Sample 8<br>2 | Sample 8<br>1 |
| F | Sample 4<br>1 | Sample 4<br>2 | Sample 4<br>4 | Sample 4<br>8 | Sample 4<br>16 | Sample 4<br>32 | Sample 9<br>32 | Sample 9<br>16 | Sample 9<br>8 | Sample 9<br>4 | Sample 9<br>2 | Sample 9<br>1 |
| G | Sample 5<br>1 | Sample 5<br>2 | Sample 5<br>4 | Sample 5<br>8 | Sample 5<br>16 | Sample 5<br>32 | Sample 10<br>32 | Sample 10<br>16 | Sample 10<br>8 | Sample 10<br>4 | Sample 10<br>2 | Sample 10<br>1 |
| H | Blank | Blank | Blank | Blank | Blank | Blank | Blank | Blank | Blank | Blank | Blank | Blank |

FIG. 13

|   | 1 | 2 | 3 | 4 | 5 | 6 | 7 | 8 | 9 | 10 | 11 | 12 |
|---|---|---|---|---|---|---|---|---|---|---|---|---|
| A | Sample 1<br>1 | Sample 1<br>2 | Sample 1<br>4 | Sample 1<br>8 | Sample 1<br>16 | Sample 1<br>32 | Sample 6<br>32 | Sample 6<br>16 | Sample 6<br>8 | Sample 6<br>4 | Sample 6<br>2 | Sample 6<br>1 |
| B | Control<br>1 | Control<br>2 | Control<br>4 | Control<br>8 | Control<br>16 | Control<br>32 | Control<br>32 | Control<br>16 | Control<br>8 | Control<br>4 | Control<br>2 | Control<br>1 |
| C | Sample 2<br>1 | Sample 2<br>2 | Sample 2<br>4 | Sample 2<br>8 | Sample 2<br>16 | Sample 2<br>32 | Sample 7<br>32 | Sample 7<br>16 | Sample 7<br>8 | Sample 7<br>4 | Sample 7<br>2 | Sample 7<br>1 |
| D | Standard<br>1 | Standard<br>2 | Standard<br>4 | Standard<br>8 | Standard<br>16 | Standard<br>32 | Standard<br>32 | Standard<br>16 | Standard<br>8 | Standard<br>4 | Standard<br>2 | Standard<br>1 |
| E | Sample 3<br>1 | Sample 3<br>2 | Sample 3<br>4 | Sample 3<br>8 | Sample 3<br>16 | Sample 3<br>32 | Sample 8<br>32 | Sample 8<br>16 | Sample 8<br>8 | Sample 8<br>4 | Sample 8<br>2 | Sample 8<br>1 |
| F | Sample 4<br>1 | Sample 4<br>2 | Sample 4<br>4 | Sample 4<br>8 | Sample 4<br>16 | Sample 4<br>32 | Sample 9<br>32 | Sample 9<br>16 | Sample 9<br>8 | Sample 9<br>4 | Sample 9<br>2 | Sample 9<br>1 |
| G | Sample 5<br>1 | Sample 5<br>2 | Sample 5<br>4 | Sample 5<br>8 | Sample 5<br>16 | Sample 5<br>32 | Sample 10<br>32 | Sample 10<br>16 | Sample 10<br>8 | Sample 10<br>4 | Sample 10<br>2 | Sample 10<br>1 |
| H | Blank | Blank | Blank | Blank | Blank | Blank | Blank | Blank | Blank | Blank | Blank | Blank |

FIG. 14

|   | 1 | 2 | 3 | 4 | 5 | 6 | 7 | 8 | 9 | 10 | 11 | 12 |
|---|---|---|---|---|---|---|---|---|---|---|---|---|
| A | Sample 1<br>1 | Sample 1<br>2 | Sample 1<br>4 | Sample 1<br>8 | Sample 1<br>16 | Sample 1<br>32 | Sample 6<br>32 | Sample 6<br>16 | Sample 6<br>8 | Sample 6<br>4 | Sample 6<br>2 | Sample 6<br>1 |
| B | Control<br>1 | Control<br>2 | Control<br>4 | Control<br>8 | Control<br>16 | Control<br>32 | Control<br>32 | Control<br>16 | Control<br>8 | Control<br>4 | Control<br>2 | Control<br>1 |
| C | Sample 2<br>1 | Sample 2<br>2 | Sample 2<br>4 | Sample 2<br>8 | Sample 2<br>16 | Sample 2<br>32 | Sample 7<br>32 | Sample 7<br>16 | Sample 7<br>8 | Sample 7<br>4 | Sample 7<br>2 | Sample 7<br>1 |
| D | Standard<br>1 | Standard<br>2 | Standard<br>4 | Standard<br>8 | Standard<br>16 | Standard<br>32 | Standard<br>32 | Standard<br>16 | Standard<br>8 | Standard<br>4 | Standard<br>2 | Standard<br>1 |
| E | Sample 3<br>1 | Sample 3<br>2 | Sample 3<br>4 | Sample 3<br>8 | Sample 3<br>16 | Sample 3<br>32 | Sample 8<br>32 | Sample 8<br>16 | Sample 8<br>8 | Sample 8<br>4 | Sample 8<br>2 | Sample 8<br>1 |
| F | Sample 4<br>1 | Sample 4<br>2 | Sample 4<br>4 | Sample 4<br>8 | Sample 4<br>16 | Sample 4<br>32 | Sample 9<br>32 | Sample 9<br>16 | Sample 9<br>8 | Sample 9<br>4 | Sample 9<br>2 | Sample 9<br>1 |
| G | Sample 5<br>1 | Sample 5<br>2 | Sample 5<br>4 | Sample 5<br>8 | Sample 5<br>16 | Sample 5<br>32 | Sample 10<br>32 | Sample 10<br>16 | Sample 10<br>8 | Sample 10<br>4 | Sample 10<br>2 | Sample 10<br>1 |
| H | Blank | Blank | Blank | Blank | Blank | Blank | Blank | Blank | Blank | Blank | Blank | Blank |

*FIG. 15*

METHOD FOR ASSAYING THE ANTIOXIDANT CAPACITY OF A SKIN CARE PRODUCT

FIELD OF THE INVENTION

The subject invention relates to a method for assaying the antioxidant capacity of a skin care product.

BACKGROUND OF THE INVENTION

Reactive oxygen species (ROS) and reactive nitrogen species (RNS) include oxygen ions, free radicals, peroxides, and the like, which are highly reactive due to the presence of unpaired valence shell electrons. Several predominant ROS/NOS in the environment include peroxyl radicals, hydroxyl radicals, superoxide, singlet oxygen, and peroxynitrile. The human skin is highly susceptible to such ROS/NOS in the environment and exposure to ROS/NOS is known to produce detrimental effects to human skin. Antioxidants are ROS/NOS scavengers which function by offering easy electron targets for ROS/NOS. By absorbing ROS/NOS, antioxidants provide a defense against ROS/NOS in the environment.

Manufacturers are now beginning to add antioxidants to skin care products, e.g., cosmetics, sun tanning oils, sun screen products, and the like, as a defense to the damaging predominant ROS/NOS in the environment. As a result, manufacturers of skin care products, and the consumers that use them, often like to know the antioxidant capacity of a particular skin care product. Because skin care products are often manufactured with unique and proprietary chemical formulations and are applied directly to the surface of the skin, the manufacturer and/or consumer needs to know the antioxidant capacity of the skin care product as it exists in its manufactured form and as it is applied to the skin.

Conventional methods for assaying the antioxidant capacity of a sample, such as those disclosed in U.S. Pat. No. 7,132,296 by one or more of the inventors hereof, incorporated by reference herein, rely on preparing a sample for testing in which by various chemicals, solubility enhancing compounds, extraction solutions, and the like are added to the sample. Such a technique typically alters or destroys the proprietary chemical formulation of the skin care product and thus does not provide a true measurement of the antioxidant of the skin care product as it is manufactured and as it is applied to the skin. Moreover, conventional methods for measuring the antioxidant capacity of a sample typically utilize a single probe which is sensitive to only one type of ROS/NOS. Thus, these conventional methods can only provide the antioxidant capacity for a one type of ROS/NOS.

Moreover, one theory on aging indicates the human skin ages because the cells in the skin accumulate ROS/NOS over time. Thus, there is a need for a panel of assays, or an anti-aging protection factor score, which can provide a true measurement of the antioxidant capacity of a skin care product for the predominant ROS/NOS in the environment.

BRIEF SUMMARY OF THE INVENTION

It is therefore an object of this invention to provide a method for assaying the antioxidant capacity of a skin care product.

It is therefore an object of this invention to provide a method for assaying the antioxidant capacity of a skin care product while maintaining the integrity of the formulation of the skin care product.

It is a further object of this invention to provide such a method which measures the antioxidant capacity of a skin care product without altering or destroying the formulation of the skin care product.

It is a further object of this invention to provide such a method which measures the antioxidant capacity of a skin care product as it is actually applied to the skin.

It is a further object of this invention to provide such a method which measures the antioxidant capacity of a skin care product for the predominant ROS/NOS in the environment.

It is a further object of this invention to provide such a method which provides a panel of assays which measure the antioxidant capacity of a skin care product for the predominant ROS/NOS in the environment.

It is a further object of this invention to provide such a method which provides an anti-aging protection factor score.

The subject invention, however, in other embodiments, need not achieve all these objectives and the claims hereof should not be limited to structures or methods capable of achieving these objectives.

This invention features a method for assaying the antioxidant capacity of a skin care product, the method including preparing an emulsion base, dissolving a sample of a skin care product into the emulsion base to form a homogeneous emulsion mixture, adding a detection probe to the homogeneous emulsion mixture, adding reactive oxygen species generator and/or a reactive nitrogen species generator to the homogeneous emulsion mixture, measuring the fluorescence intensity change of the detection probe in the presence of the sample over time, in the presence of the standard over time, and in the presence of a blank over time, and calculating the initial rate of oxidation of the detection probe to determine the antioxidant capacity of the sample of the skin care product.

In one embodiment, the detection probe may be a non-protein probe. The non-protein probe may include a hydrogen atom donor probe. The detection probe may be chosen from the group consisting of dihydrorhodamine-6G, methyl 2-(3,6-diamino-9H-xanthene-9-yl)benzoate (dihydrorhodamine-123), and 5-ethyl-5,6-dihydro-6-phenyl-3,8-phenanthridinediamine(hydroethidine). The detection probe may be chosen for a predetermined reactive oxygen species and/or a predetermined reactive nitrogen species. The detection probe may include dihydrorhodamine-6G and the reactive oxygen species including peroxyl radicals. The detection probe may include dihyrohodamine-6G and the hydroxyl reactive oxygen species may include hydroxyl radicals. The detection probe may include methyl 2-(3,6-diamino-9H-xanthene-9-yl)benzoate and the reactive nitrogen species may include peroxynitrites. The detection probe may include 5-ethyl-5,6-dihydro-6-phenyl-3,8-phenanthridinediamine and the reactive oxygen species may include superoxide anions. The detection probe may include 5-ethyl-5,6-dihydro-6-phenyl-3,8-phenanthridinediamine and the reactive oxygen species may include singlet oxygen. The reactive oxygen species generator and/or the reactive nitrogen species may be chosen to generate the predetermined reactive oxygen species and/or the predetermined reactive nitrogen species. The reactive oxygen species generator may include 2,2-Azobis(2-amidino-propane)dihydrochloride (AAPH) and the reactive oxygen species may include peroxyl radicals. The reactive oxygen species generator may include a combination of cobalt fluoride, picolinic acid, and hydrogen peroxide and the reactive oxygen species may include hydroxyl radicals. The reactive nitrogen species generator may include 3-morpholino-syndnonimine hydrochloride and the reactive nitrogen species may include peroxynitrites. The reactive oxygen species generator may include a combination of xanthin and xanthin oxidase and the reactive oxygen species may include superoxide anions. The reactive oxygen species generator may include a combination of lithium molybate, sodium hydroxide, and hydrogen peroxide and the reactive oxygen species may include singlet oxygen. The sample may be dissolved in the emulsion base by vortex mixing. The sample may be dissolved in the emulsion base using an emulsifier. The emulsion base may be comprised of a combination of an oil, water, and a surfactant. The standard may have a known antioxidant capacity. The standard may include Vitamin E. The standard may include a mixture of the detection probe, the chemical having a known antioxidant capacity, and the emulsion base. The blank may include a mixture of the detection probe and the emulsion base. Assaying the antioxidant capacity of a sample may include an assay chosen from the group consisting of: an Oxygen Radical Absorbance Capacity (ORAC) assay, a Hydroxy Radical Averting Capacity (HORAC) assay, a No Radical Absorbance Capacity (NORAC) assay, a Super Oxide Radical Absorbance Capacity (SORAC), and a Singlet Oxygen Absorbance Capacity (SOAC).

This invention also features a method for assaying the antioxidant capacity of a skin care product while maintaining the integrity of the formulation thereof, the method including preparing an emulsion base, dissolving a sample of a skin care product into the emulsion base to form a homogeneous emulsion mixture, adding a detection probe to the homogeneous emulsion mixture, adding reactive oxygen species generator and/or a reactive nitrogen species generator to the homogeneous emulsion mixture, measuring the fluorescence intensity change of the detection probe in the presence of the sample over time, in the presence of the standard over time, and in the presence of a blank over time, and calculating the initial rate of oxidation of the detection probe to determine the antioxidant capacity of the sample of the skin care product.

This invention also features a method for assaying an anti-aging protection factor for a skin care product, the method including preparing a plurality of emulsions bases, dissolving a sample of a skin care product into each of the plurality of emulsion bases to form a plurality of homogeneous emulsion mixtures, adding a predetermined detection probe specific for a predetermined reactive oxygen species and/or a predetermined reactive nitrogen species to each of the plurality homogeneous emulsion mixtures, adding reactive oxygen species generator and/or a reactive nitrogen species specific for each of the predetermined reactive oxygen species and/or the predetermined nitrogen species to each of the plurality of homogeneous emulsion mixtures, measuring the fluorescence intensity change of each of the predetermined detection probes in the presence of each sample in the presence of a standard, and in the presence of a blank over time, and calculating the initial rate of oxidation of each of the predetermined detection probes to determine the antioxidant capacity of the sample of the skin care product in each of the plurality of homogeneous emulsion mixtures and provide an anti-aging protection factor score.

In one embodiment, the antioxidant capacity of the skin care product in each of the plurality of homogeneous emulsion mixtures may be summed to provide an anti-aging protection factor score. The anti-aging protection score may be generated by a combination of one or more of: an Oxygen Radical Absorbance Capacity (ORAC) assay, a Hydroxy Radical Averting Capacity (HORAC) assay, a NORAC No Radical Absorbance Capacity (NORAC) assay, a Super Oxide Radical Absorbance Capacity (SORAC), and a Singlet Oxygen Absorbance Capacity (SOAC). The detection probe may be a non-protein probe. The non-protein probe may include a hydrogen atom donor probe. The detection probe may be chosen from the group consisting of: dihydrorhodamine-6G, methyl 2-(3,6-diamino-9H-xanthene-9-yl) benzoate (dihydrorhodamine-123), and 5-ethyl-5,6-dihydro-6-phenyl-3,8-phenanthridinediamine(hydroethidine). The detection probe may be chosen for a predetermined reactive oxygen species and/or a predetermined reactive nitrogen species. The detection probe may include dihydrorhodamine-6G and the reactive oxygen species may include peroxyl radicals. The detection probe may include dihydrorhodamine-6G and the hydroxyl reactive oxygen species may include hydroxyl radicals. The detection probe may include methyl 2-(3,6-diamino-9H-xanthene-9-yl)benzoate and the reactive nitrogen species may include peroxynitrites. The detection probe may include 5-ethyl-5,6-dihydro-6-phenyl-3,8-phenanthridinediamine and the reactive oxygen species may include superoxide anions. The detection probe may include 5-ethyl-5,6-dihydro-6-phenyl-3,8-phenanthridinediamine and the reactive oxygen species may include singlet oxygen. The reactive oxygen species generator and/or the reactive nitrogen species may be chosen to generate the predetermined reactive oxygen species and/or the predetermined reactive nitrogen species. The reactive oxygen species generator may include 2,2-Azobis(2-amidino-propane)dihydrochloride (AAPH) and the reactive oxygen species may include peroxyl radicals. The reactive oxygen species generator may include a combination of cobalt fluoride, picolinic acid and hydrogen peroxide and the reactive oxygen species may include hydroxyl radicals. The reactive nitrogen species generator may include 3-morpholinosyndnonimine hydrochloride and the reactive nitrogen species may include peroxynitrites. The reactive oxygen species generator may include a combination of xanthin and xanthin oxidase and the reactive oxygen species may include superoxide anions. The reactive oxygen species generator may include a combination of lithium molybate, sodium hydroxide, and hydrogen peroxide and the reactive oxygen species may include singlet oxygen. The sample may be dissolved in each of the emulsion bases by vortex mixing. The sample may be dissolved in each of the emulsion bases using an emulsifier. Each of the plurality of emulsion bases may be comprised of a combination of an oil, water, and a surfactant. The standard may have a known antioxidant capacity. The standard may include Vitamin E. The standard may include a mixture of the detection probe, a chemical having a known antioxidant capacity, and the emulsion base. The blank may include a mixture of the detection probe and the emulsion base.

In one embodiment, the antioxidant capacity of the skin care product in each of the plurality of homogeneous emulsion mixtures may be summed to provide an anti-aging protection factor score. The anti-aging protection score may be generated by a combination of one or more of an Oxygen Radical Absorbance Capacity (ORAC) assay, a Hydroxy Radical Averting Capacity (HORAC) assay, a No Radical Absorbance Capacity (NORAC) assay, a Super Oxide Radical Absorbance Capacity (SORAC), and a Singlet Oxygen Absorbance Capacity (SOAC).

This invention further features a method for assaying an anti-aging protection factor for a skin care product while maintaining the integrity of the formulation thereof the method including preparing a plurality of emulsions bases, dissolving a sample of a skin care product into each of the plurality of emulsion bases to form a plurality of homogeneous emulsion mixtures, adding a predetermined detection probe specific for a predetermined reactive oxygen species and/or a predetermined reactive nitrogen species to each of the plurality homogeneous emulsion mixtures, adding reactive oxygen species generator and/or a reactive nitrogen species specific for each of the predetermined reactive oxygen species and/or the predetermined nitrogen species to each of the plurality of homogeneous emulsion mixtures, measuring the fluorescence intensity change of each of the predetermined detection probes in the presence of each sample in the presence of a standard, and in the presence of a blank over time, and calculating the initial rate of oxidation of each of the predetermined detection probes to determine the antioxidant capacity of the sample of the skin care product in each of the plurality of homogeneous emulsion mixtures and provide an anti-aging protection factor score.

In one embodiment, the antioxidant capacity of the skin care product in each of the plurality of homogeneous emulsion mixtures may be summed to provide an anti-aging protection factor score. The anti-aging protection score may be generated by a combination of one or more of: an Oxygen Radical Absorbance Capacity (ORAC) assay, a Hydroxy Radical Averting Capacity (HORAC) assay, a NORAC No Radical Absorbance Capacity (NORAC) assay, a Super Oxide Radical Absorbance Capacity (SORAC), and a Singlet Oxygen Absorbance Capacity (SOAC).

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 11 is a schematic diagram showing one example of the layout of the 96-well microplate at station E shown in FIG. 10 used in the Example Section of this invention;

FIG. 12 is a schematic diagram showing one example of the layout of the 96-well microplate for HORAC assay at station E shown in FIG. 10 used in the Example Section of this invention;

FIG. 13 is a schematic diagram showing one example of the layout of the 96-well microplate for NORAC assay at station E shown in FIG. 10 used in the Example Section of this invention;

FIG. 14 is a schematic diagram showing one example of the layout of the 96-well microplate for SORAC assay at station E; shown in FIG. 10 used in the Example Section of this invention; and FIG. 15 is a schematic diagram showing one example of the layout of the 96-well microplate for SOAC assay at station E shown in FIG. 10 used in the Example Section of this invention.

DETAILED DESCRIPTION OF THE INVENTION

Figure 1:
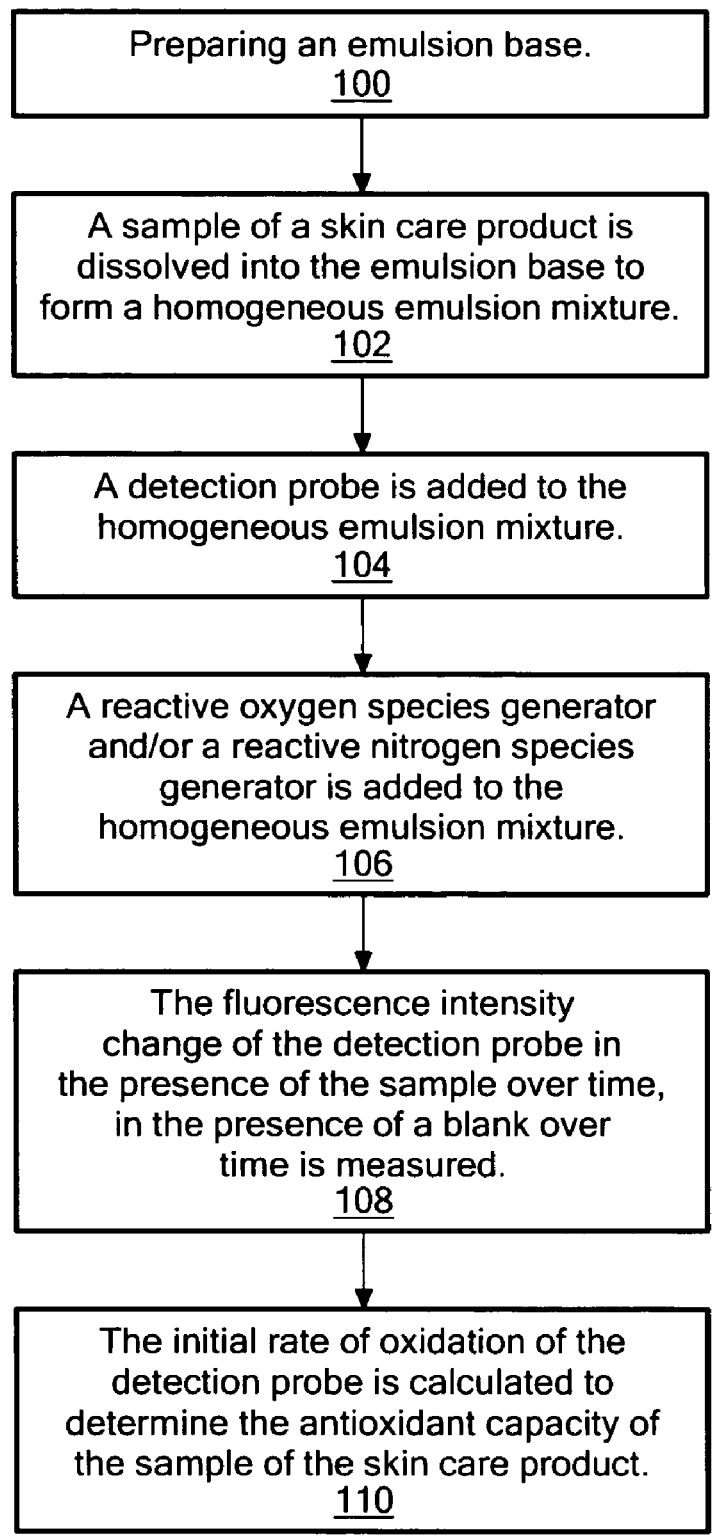
FIG. 1 is a schematic block diagram showing the primary steps associated with the one embodiment of the method for assaying the antioxidant capacity of a skin care product of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

As discussed in the Background section above, conventional methods for assaying the antioxidant capacity of a sample typically rely on preparing a sample for testing in which various chemicals, solubility enhancing compounds, extraction solution, and the like, are added to the sample. However, such a technique alters or destroys the chemical formulation of the sample. Thus, conventional methods for assaying an antioxidant capacity of a sample cannot be used to test the antioxidant of skin care products. Moreover, conventional methods for assaying the antioxidant capacity of a sample use only a single probe which is sensitive to one type of ROS/NOS.

In contrast, the inventors hereof have developed a new method for assaying the antioxidant capacity of a skin care product which maintains the integrity of the formulation of the skin care product and accommodates testing the antioxidant capacity of the skin care product for the predominant ROS/NOS present in the environment typically of concern to skin care product manufactures and consumers. The method uses an array of detection probes which are chosen for the predominant ROS/NOS present in the environment. The corresponding ROS/NOS generator is then chosen for the particular detection probe.

One embodiment of the subject invention provides a panel of assays which can measure the antioxidant capacity of the skin care product to the predominant ROS/NOS present in the environment, referred to by the inventor hereof as an "anti-aging protection factor" (APF) score. Table 1 below summarizes exemplary ROS/NOS, detection probes, ROS/NOS generators, and the assay names utilized by the method for assaying the antioxidant capacity of a skin care product of this invention.

TABLE 1

| ROS/NOS | ROS/NOS Generator | Assay name | Detection Probe (trade name) |
|---|---|---|---|
| peroxyl radicals | 2,2-Azobis (2-amidino-propane) dihydrochloride | ORAC | Dihydro-rhodamine-6G |
| hydroxyl radicals | cobalt fuloride/picolinic acid/hydrogen peroxide | HORAC | Dihydro-rhodamine-6G |
| Peroxy-nitrites | 3-morpholinosyndnonimine hydrochloride | NORAC | Dihydro-rhodamine-123 |
| superoxide anions | Xanthine/Xanthine oxidase | SORAC | hydroethidine |
| singlet oxygen | Lithium Molybate/sodium hydroxide/hydrogen peroxide | SOAC | hydroethidine |

One embodiment of the method for assaying the antioxidant capacity of a skin care product of this invention includes preparing an emulsion base, step 100, FIG. 1. A sample of the skin care product is dissolved into the emulsion base to form a homogeneous emulsion mixture, step 102. In one example, a sample of the skincare product is dissolved in the emulsion base by vortex mixing or with an emulsifier. The emulsion base is typically comprised of oil, e.g., methyl cis,cis-9,12-octadecadienoate (methyl linoleate), water, and surfactant, such as polyoxyethylene (20) sorbitan monolaurate (Tween 20). The emulsion base is formulated so it does not alter or destroy the chemical formulation of the sample of the skincare product. Other emulsion base mixtures which do not alter the formulation of the skin care product may be used, as known to those skilled in the art, e.g., oil, water and sodium dodecyl sulfate, oil, water and cetyl trimethylammonium bromide, oil, water and dodecyl betaine, and the like.

A detection probe is then added to the homogeneous emulsion mixture, step 104. The detection probe is ideally a non-protein probe. The non-protein probe is preferably a hydrogen atom donor probe, as discussed in further detail below. The detection probe is chosen for a predetermined ROS/NOS, e.g., any of the predominant ROS/NOS in the environment, such as those shown in Table 1 above. Other non-protein probes for other ROS/NOS may also be used, as known to those skilled in the art.

A reactive oxygen species generator and/or a reactive nitrogen species generator is then added to the homogeneous emulsion mixture, step 106. The ROS and/or the NOS species generator is chosen to generate the ROS/NOS chosen in step 104.

The fluorescence intensity change of the detection probe in the presence of the standard over time, in the presence of the sample over time, and in the presence of the blank over time, is measured, step 108. The standard typically includes a mixture of the detection probe, the standard, and the emulsion base. A standard is utilized which has a known antioxidant capacity, e.g., 2,5,7,8-Tetramethyl-2-(4',8',12'-trimethyl-tridecyl)-6-chromanol (Vitamin E). The blank is preferably a mixture of the detection probe and the emulsion base.

Figure 2:
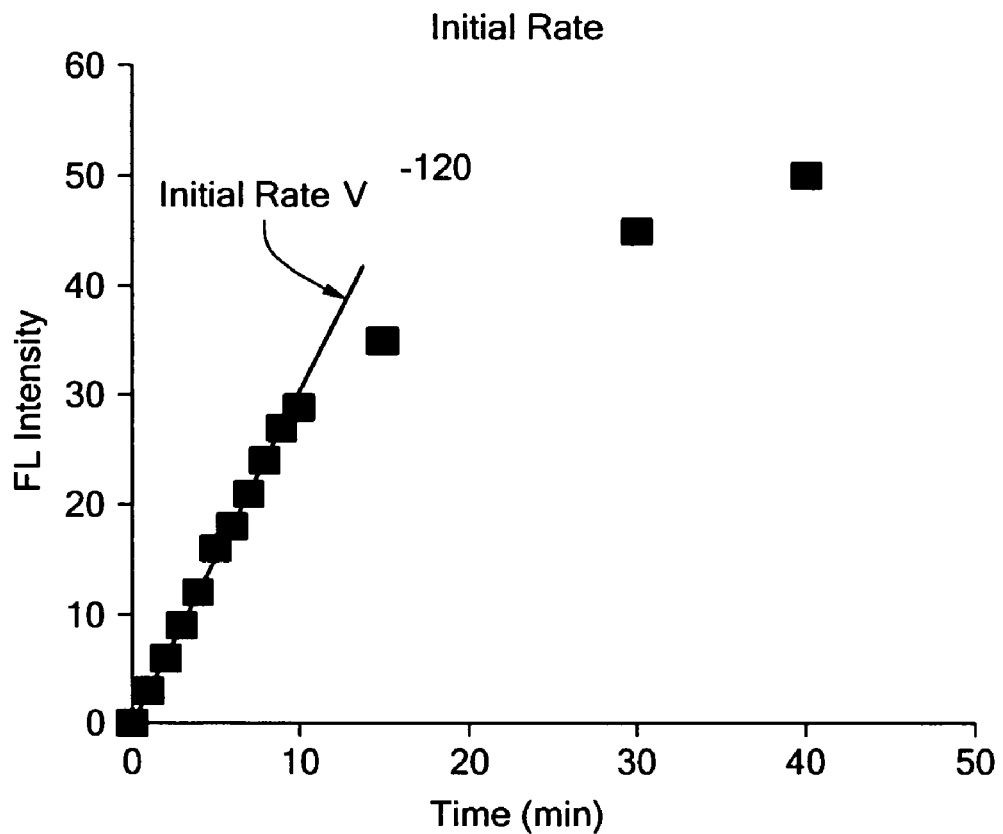
FIG. 2 shows a graph of an example of the slope of the propagation phase and a fluorescence base at an initial time used to calculate the antioxidant capacity of a skin care product in accordance with this invention.
Figure 3:
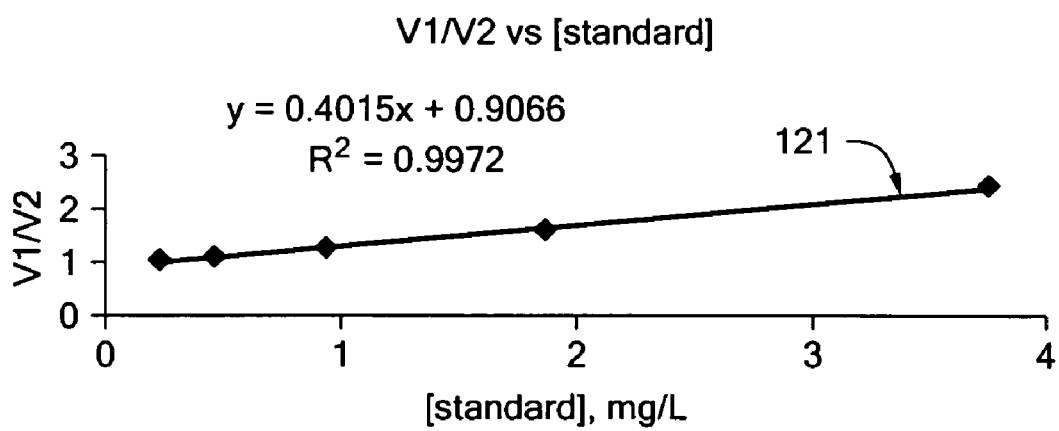
FIG. 3 shows an example of a linear curve for one example of a standard utilized by the method for assaying the antioxidant capacity of a skin care product of this invention.

The initial rate of oxidation of the detection probe is then calculated to determine the antioxidant capacity of the sample of the skin care product, step 110. For example, the initial rate V-120, FIG. 2, is defined as the slope of the propagation phase and the fluorescence base at initial period. It is assumed that ROS/NOS is generated constantly by the ROS/NOS generator. The rate of ROS/NOS production is constant and pseudo-zero. The ROS/NOS formed either reacts with the detection probe or is scavenged by antioxidant in the sample of the skin care product. The combination of the probe and the ROS/NOS produces an oxidized probe. The combination of the ROS/NOS and the antioxidant produces an oxidized antioxidant. Assuming a steady state concentration of the ROS/NOS, the rate of ROS/NOS consumption without an antioxidant is defined by equation (1):

$$-\frac{d[ROS/NOS]_1}{dt} = k_{probe}[\text{probe}]_1[ROS/NOS]_1 \tag{1}$$

The rate of ROS/NOS consumption with the antioxidant concentration is defined by equation (2):

$$-\frac{d[ROS/NOS]_2}{dt} = k_{probe}[\text{probe}]_2[ROS/NOS]_2 + k_{antioxidant}[\text{antioxidant}]_2[ROS/NOS]_2) \tag{2}$$

Because the rate of ROS/NOS consumption is determined only by ROS/NOS source generator, equation (3) below is valid:

$$-\frac{d[ROS/NOS]_1}{dt} = -\frac{d[ROS/NOS]_2}{dt} \tag{3}$$

On the other hand, the fluorescence increase rates in the absence ($V_1$) and presence ($V_2$) of antioxidant are defined by equations (4) and (5) below, respectively:

$$V_1 = k_{probe}[\text{probe}]_1[ROS/NOS]_1 \tag{4}$$

$$V_2 = k_{probe}[\text{probe}]_2[ROS/NOS]_2 \tag{5}$$

From equations (5) and (6), $V_1$ can be rewritten as:

$$V_1 = k_{probe}[\text{probe}]_2[ROS/NOS]_2 + k_{antioxidant}[\text{Antioxidant}]_2[ROS/NOS]_2 \tag{6}$$

Therefore, the fluorescence increase rates in the absence ($V_1$) and in the presence ($V_2$) of the antioxidant have the following relationship:

$$\frac{V_1}{V_2} = 1 + \frac{k_{antioxidant}[\text{Antioxidant}]}{k_{[probe]}[\text{probe}]_2} \tag{7}$$

A plot of $$\frac{V_1}{V_2}$$

versus antioxidant will give a linear curve with interception at (0, 1) and the slope of $k_{antioxidant}/k_{probe}[\text{probe}]_2$. FIG. 2 shows such an exemplary plot 121 for the standard over time. The slope of k is a reflection of the antioxidant capacity of the sample of the skin care product. The larger the slope, the higher antioxidant capacity. The individual antioxidant capacity of the sample is defined in accordance with equation (8) below:

$$\text{Antioxidant capacity} = k_{Sample}/k_{standard} \tag{8}$$

Figure 4:
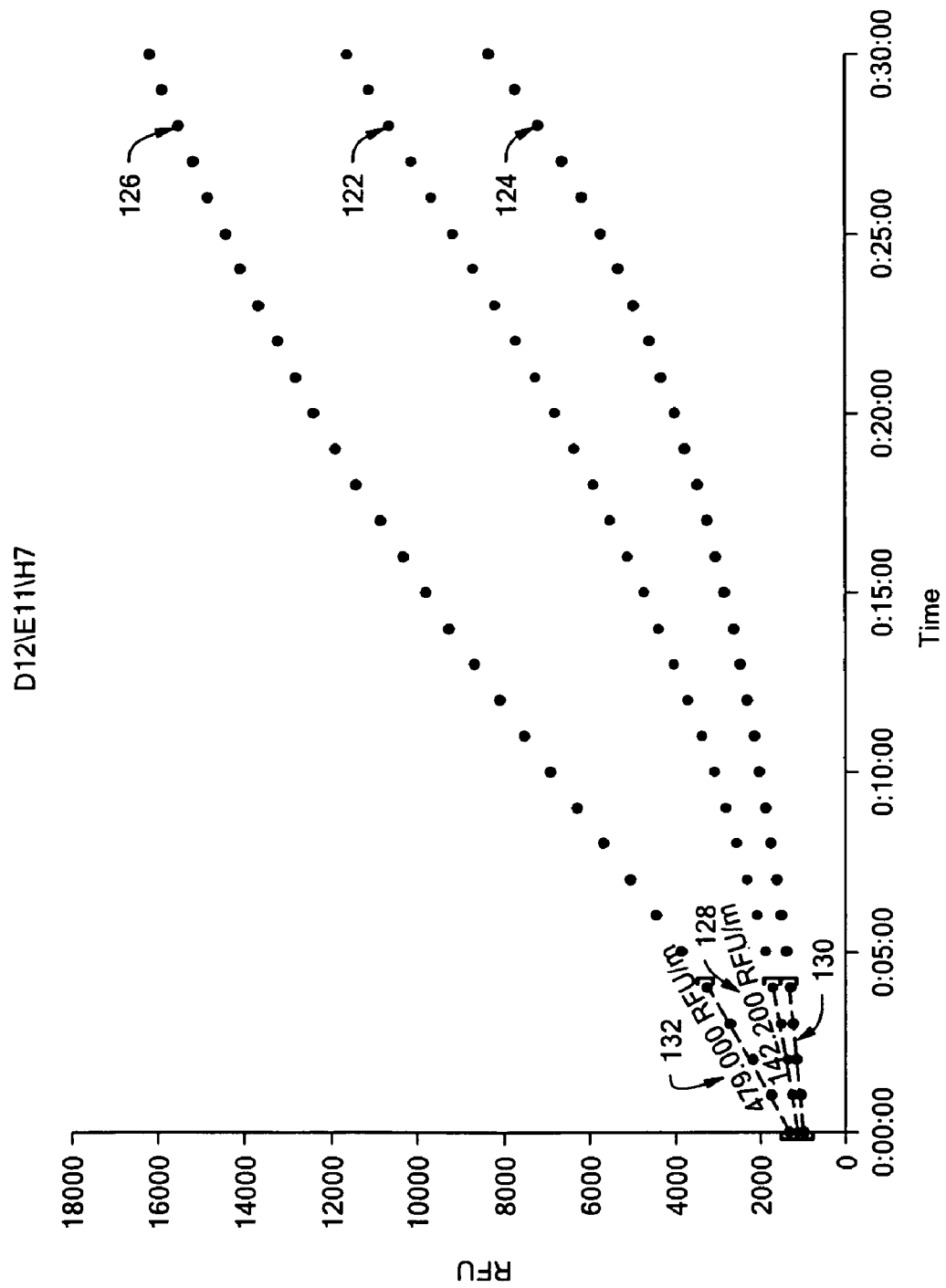
FIG. 4 is a graph showing the fluorescence intensity change of a sample, a standard and a blank used to calculate the antioxidant capacity of a skin care product in accordance with the ORAC assay embodiment of the method of this invention.

FIG. 4 shows an example of the Oxygen Radical Absorbance Capacity (ORAC) assay utilized for measuring the antioxidant capacity of a skin care product to the peroxyl radicals using the corresponding ROS generator and the detection probe shown in Table 1. The fluorescence intensity change of the detection probe in the presence of the sample over time is shown by curve 122. The fluorescence intensity of the detection probe in the presence of the standard over time is shown by curve 124. In this example, the standard is 370 μm Vitamin E. The fluorescence intensity change of the detection probe in the presence of the blank over time is shown by curve 126. The initial rate of oxidation of the detection probe is calculated from slopes of the linear curve 128 for the sample, linear curve 130 for the standard, and linear curve 132 for the blank using equations (1) to (8) discussed above to determine the antioxidant capacity of the sample of the skin care product.

Figure 5:
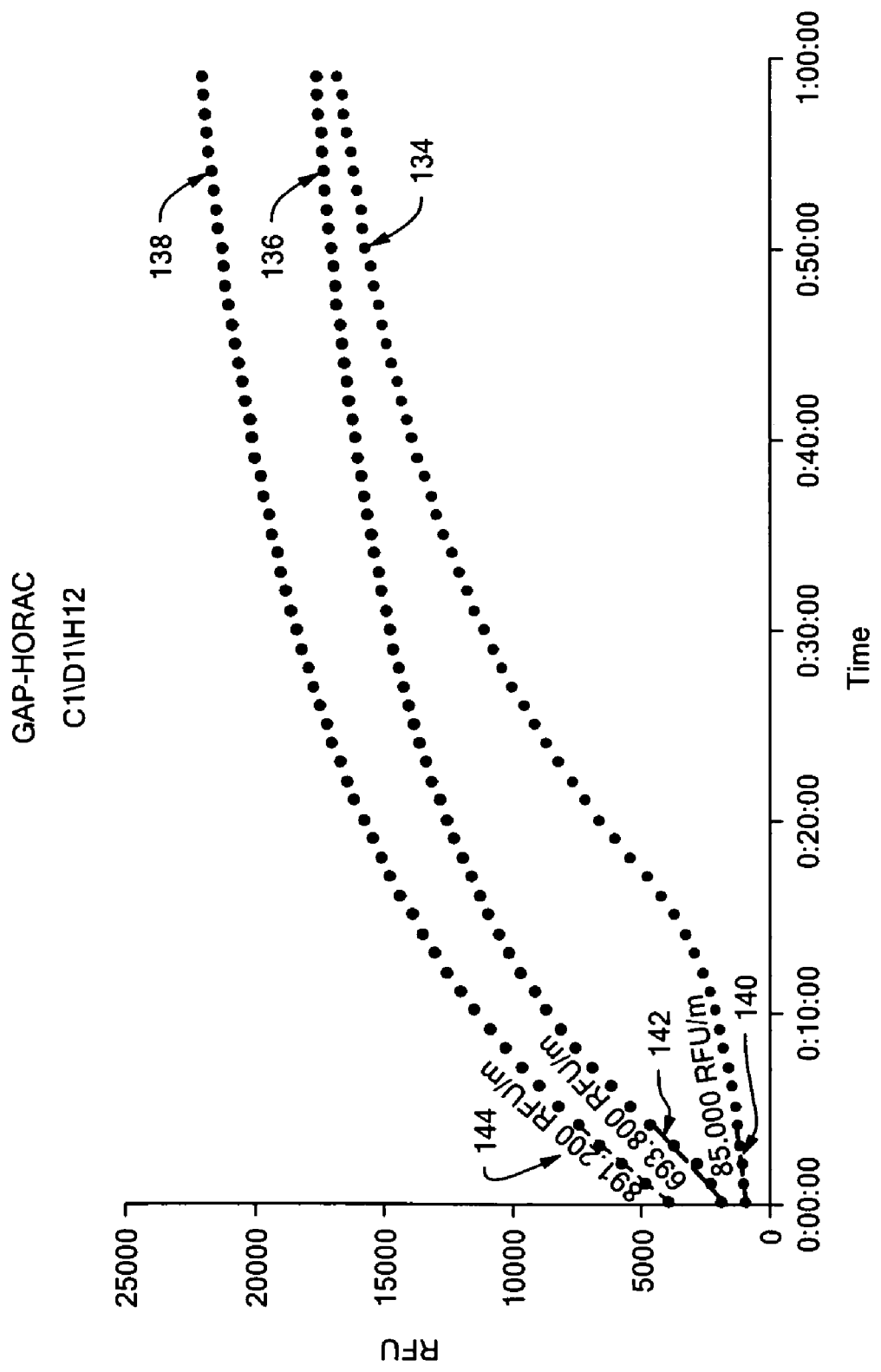
FIG. 5 is a graph showing the fluorescence intensity change of a sample, a standard and a blank used to calculate the antioxidant capacity of a skin care product in accordance with the HORAC assay embodiment of the method of this invention.

FIG. 5 shows an example of the Hydroxy Radical Averting Capacity (HORAC) assay utilized for measuring the antioxidant capacity of a skin care product to hydroxyl radicals using the corresponding ROS generator and the detection probe shown in Table 1. The fluorescence intensity change of the detection probe in the presence of the sample over time is shown by curve 134. The fluorescence intensity of the detection probe in the presence of the standard over time is shown by curve 136. In this example, the standard is 18.60 mM Vitamin E. The fluorescence intensity change of the detection probe in the presence of the blank over time is shown by curve 138. The initial rate of oxidation of the detection probe is calculated from slopes of the linear curve 140 for the sample, linear curve 142 for the standard, and linear curve 144 for the blank using equations (1) to (8) above to determine the antioxidant capacity of the sample of the skin care product.

Figure 6:
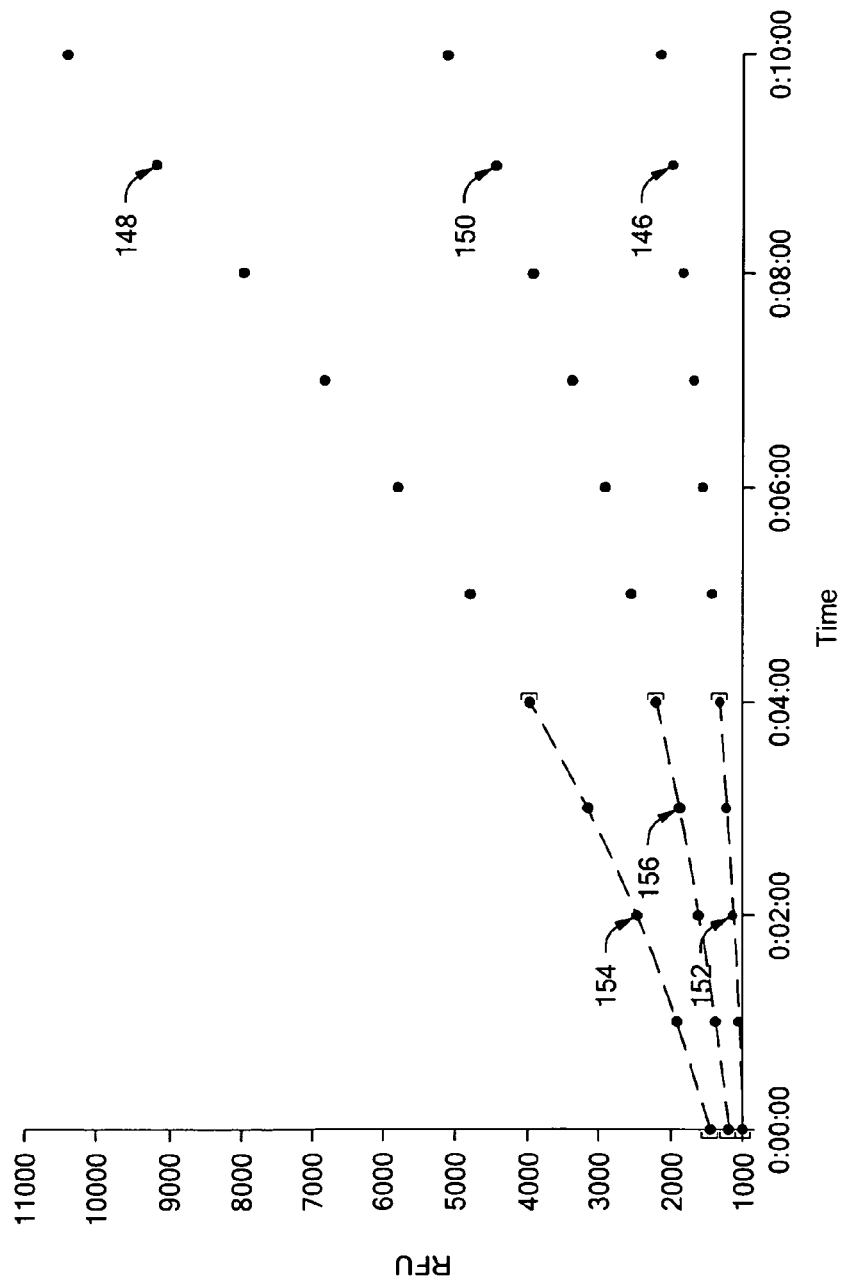
FIG. 6 is a graph showing the fluorescence intensity change of a sample, a standard and a blank used to calculate the antioxidant capacity of a skin care product in accordance with the NORAC assay embodiment of the method of this invention.

FIG. 6 shows an example of the No Radical Absorbance Capacity (NORAC) assay utilized for assaying the antioxidant capacity of a skin care product to the peroxynitrites using the corresponding NOS generator and the detection probe shown in Table 1. The fluorescence intensity change of the detection probe in the presence of the sample over time is shown by curve 146. The fluorescence intensity of the detection probe in the presence of the standard over time is indicated by curve 148. In this example, the standard is 464 μM Vitamin E. The fluorescence intensity change of the detection probe in the presence of the blank over time is shown by curve 150. The initial rate of oxidation of the detection probe is calculated from slopes of the linear curve 152 for the sample, linear curve 154 for the standard, and linear curve 156 for the blank using equations (1) to (8) above to determine the antioxidant capacity of the sample of the skin care product.

Figure 7:
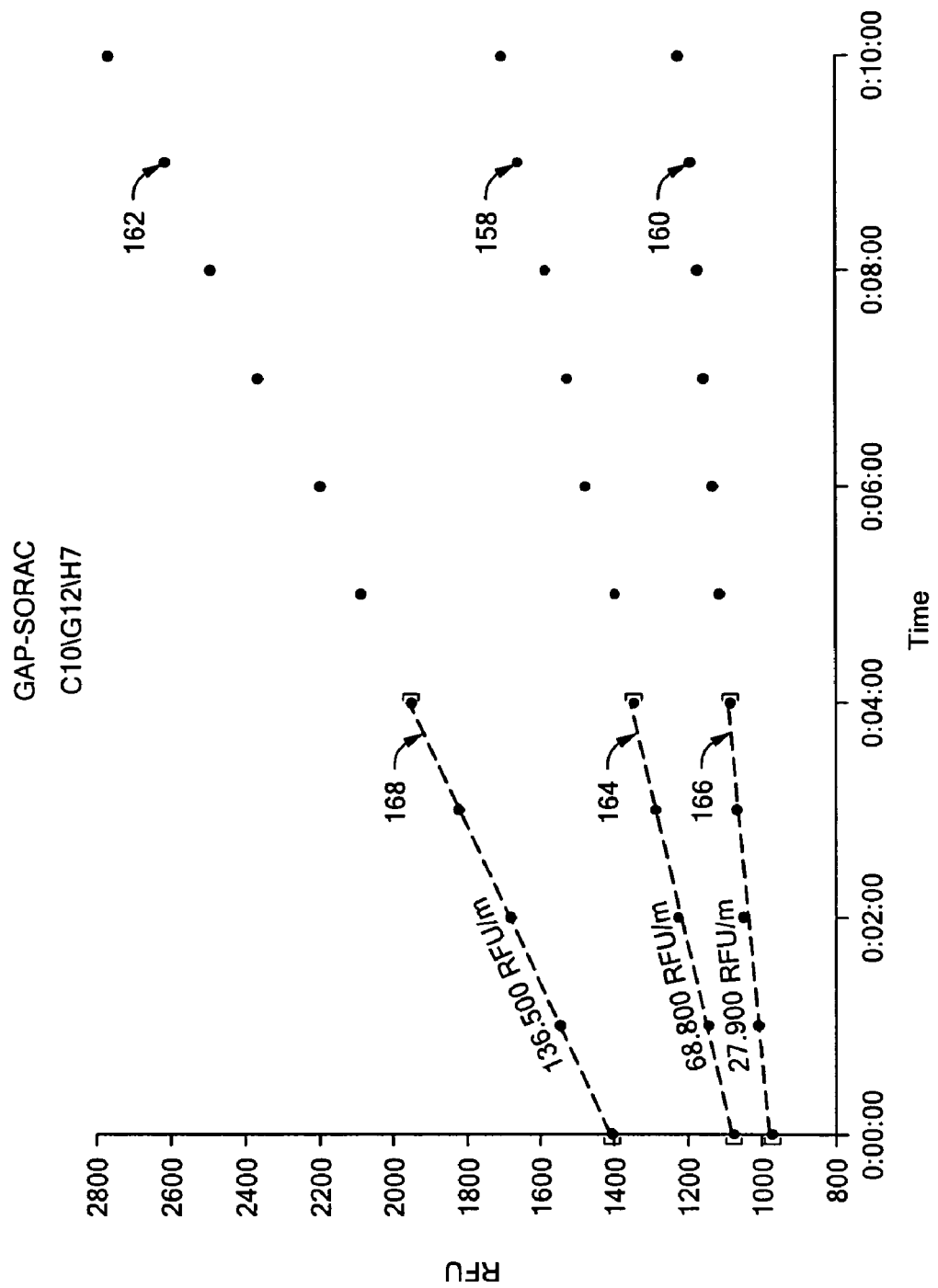
FIG. 7 is a graph showing the fluorescence intensity change of a sample, a standard and a blank used to calculate the antioxidant capacity of a skin care product in accordance with the SORAC assay embodiment of the method of this invention.

FIG. 7 shows an example of the Super Oxide Radical Absorbance Capacity (SORAC) using the corresponding ROS generator and the detection probe shown in Table 1 assay utilized for assaying the antioxidant capacity of a skin care product to the superoxide anions using the corresponding ROS generator and the detection probe shown in Table 1. The fluorescence intensity change of the detection probe in the presence of the sample over time is shown by curve 158. The fluorescence intensity of the detection probe in the presence of the standard over time is shown by cure 160. In this example, the standard is 2 μM Vitamin E. The fluorescence intensity change of the detection probe in the presence of the blank over time is shown by curve 162. The initial rate of oxidation of the detection probe is calculated from slopes of the linear curve 164 for the sample, linear curve 166 for the standard, and linear curve 168 for the blank using equations (1) to (8) above to determine the antioxidant capacity of the sample of the skin care product.

Figure 8:
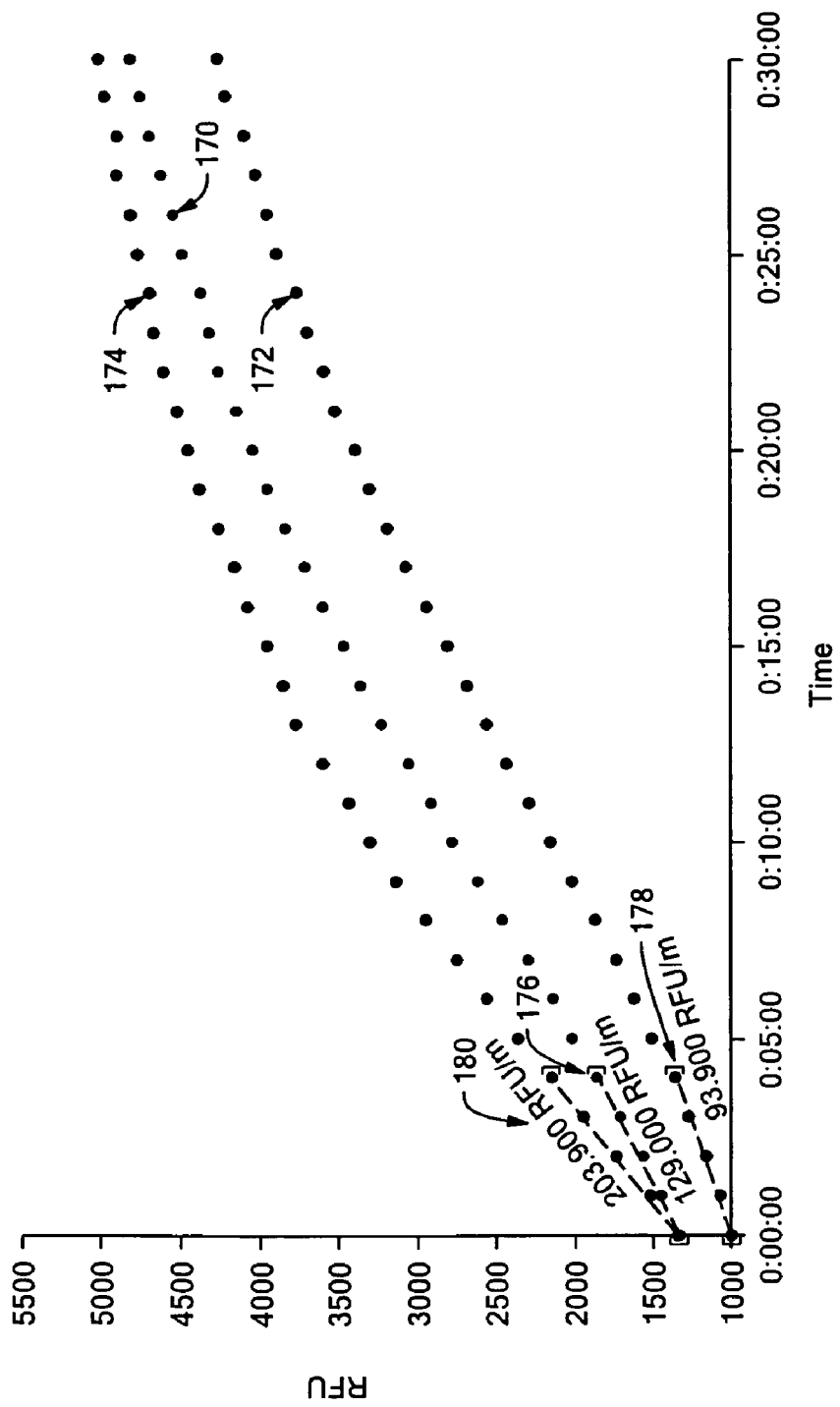
FIG. 8 is a graph showing the fluorescence intensity change of a sample, a standard and a blank used to calculate the antioxidant capacity of a skin care product in accordance with the SOAC assay embodiment of the method of this invention.

FIG. 8 shows an example of the Singlet Oxygen Absorbance Capacity (SOAC) using the corresponding ROS generator and the detection probe shown in Table 1 assay utilized for assaying the antioxidant capacity of a skin care product to the singlet oxygen using the corresponding ROS generator and the detection probe shown in Table 1. The fluorescence intensity change of the detection probe in the presence of the sample over time is shown by curve 170. The fluorescence intensity of the detection probe in the presence of the standard over time is shown by curve 172. In this example, the standard is 18.60 mM of Vitamin E. The fluorescence intensity change of the detection probe in the presence of the blank over time is by curve 174. The initial rate of oxidation of the detection probe is calculated from slopes of the linear curve 176 for the sample, linear curve 178 for the standard, and linear curve 180 for the blank, using equations (1) to (8) above to determine the antioxidant capacity of the sample of the skin care product.

As discussed above, the detection probe may be a non-protein probe which preferably includes a hydrogen atom donor probe. The detection probe may be any one of dihydrorhodamine-6G, methyl 2-(3,6-diamino-9H-xanthene-9-yl)benzoate(dihydrorhodamine-123), or 5-ethyl-5,6-dihydro-6-phenyl-3,8-phenanthridinediamine(hydroethidine) or other similar type detection probes known to those skilled in the art. The detection probe is preferably chosen for a ROS or a RNS for which the antioxidant capacity of the sample of the skin care product is measured. For example, the detection probe may be dihydrorhodamine-6G which is used to measure the antioxidant capacity of the sample of the skin care product to peroxyl radicals and/or hydroxyl radicals. The detection probe may be methyl 2-(3,6-diamino-9H-xanthene-9-yl)benzoate(dihydrorhodamine-123), which is used to measure the antioxidant capacity of the sample of the skin care product to peroxynitrites. The detection probe may be 5-ethyl-5,6-dihydro-6-phenyl-3,8-phenanthridinediamine (hydroethidine) which is used to measure the antioxidant capacity of the sample of the skin care product to superoxide anions. The detection probe may include 5-ethyl-5,6-dihydro-6-phenyl-3,8-phenanthridinediamine(hydroethidine) which is used to measure the antioxidant capacity of the sample of the skin care product to singlet oxygen. Other detection probes as known by those skilled in the art may also be utilized.

The ROS generator and/or the RNS generator is preferably chosen to generate the ROS and/or the RNS for the detection probes discussed above. For example, 2,2-Azobis(2-amidino-propane) dihydrochloride (AAPH) may be chosen to generate peroxyl radicals. A combination of cobalt fluoride, picolinic acid and hydrogen peroxide may be chosen to generate hydroxyl radicals. 3-morpholinosyndnonimine hydrochloride may be chosen to generate peroxynitrites. Xanthin and/or xanthin oxidase may be chosen to generate superoxide anions. A combination of lithium molybate, sodium hydroxide, and hydrogen peroxide may be chosen to generate singlet oxygen. See Table 1 above. Other ROS/RNS generates as known by those skilled in the art may also be utilized.

The result is the method for assaying the antioxidant capacity of a skin care product of this invention eliminates the need to add chemicals, such as solubility enhancing compounds, extraction solutions, and the like to the sample of the skin care product. Therefore, the method of assaying the antioxidant capacity of a skin care product of this invention does not alter or destroy the chemical formation of the skin care product and provides a true measurement of the antioxidant capacity of the skin care product as it is manufactured and applied to the skin. Moreover, the method for assaying the antioxidant capacity of a skin care product of this invention can test for the predominant ROS/NOS in the environment.

Figure 9:
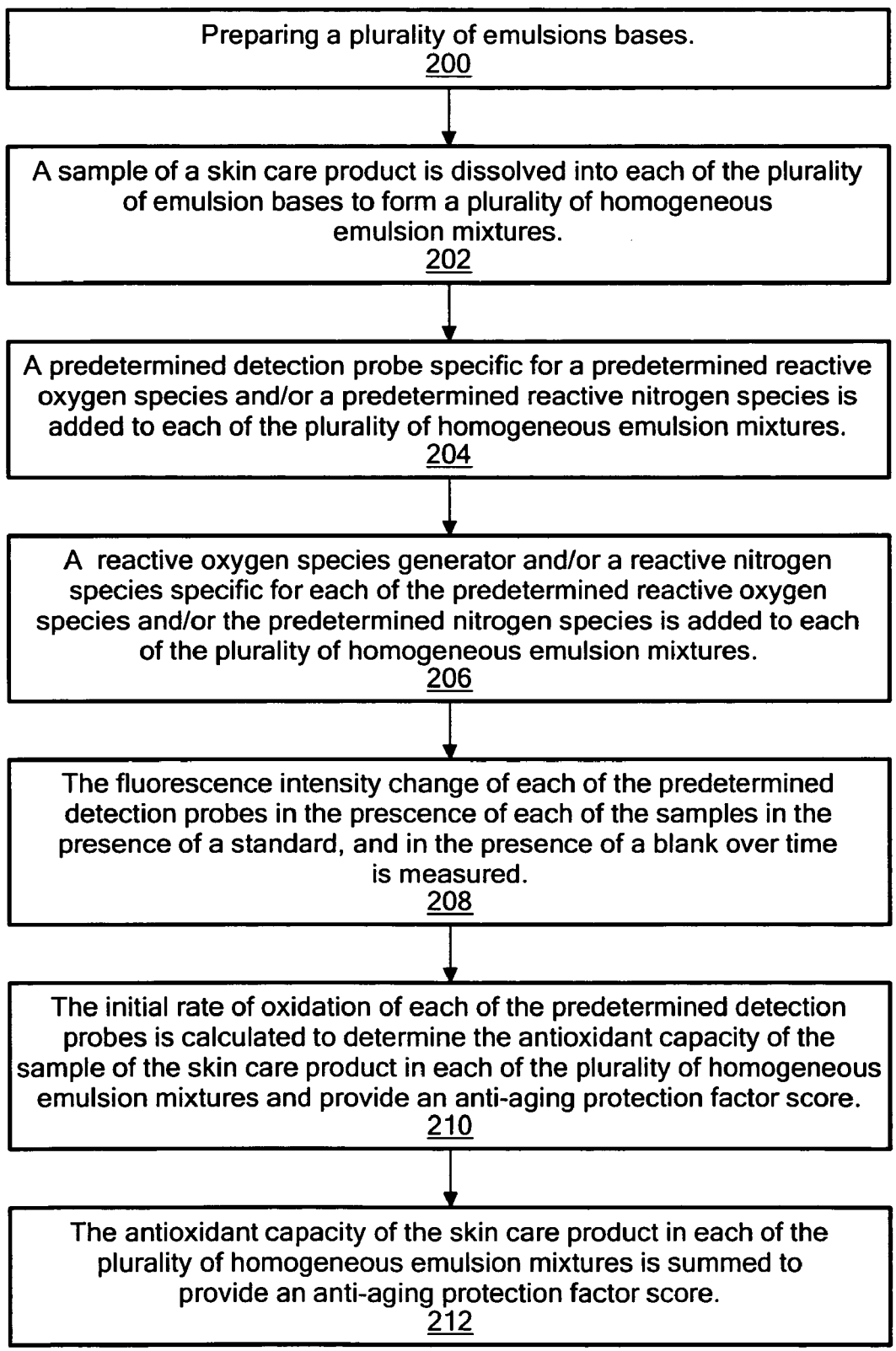
FIG. 9 is a schematic block diagram showing the primary steps associated with the one embodiment of the method of assaying the antioxidant capacity of a skin care product which includes a panel of assays used to provide an anti-aging protection factor score for a skin care product of this invention.

In order to accommodate a complete panel of antioxidant capacity assays for the prevalent ROS/NOS in the environment, another embodiment of the method for assaying an anti-aging protection factor for a skin care product of this invention includes preparing a plurality of emulsion bases, step 200, FIG. 9. A sample of the skin care product is dissolved into each of the plurality of emulsion bases to form a plurality of homogeneous emulsion mixtures, step 202. A predetermined detection probe for a specific ROS and/or a RNS is added to each of the plurality of homogeneous emulsion mixtures, step 204, e.g., as summarized in Table 1 above. A reactive oxygen species generator and/or a reactive nitrogen species generator specific for each of the predetermined reactive oxygen species and/or the predetermined reactive nitrogen species is added to each of the plurality of homogeneous emulsion mixtures, step 206. See Table 1 above. The fluorescence intensity change of each of the predetermined detection probes in the presence of each of the samples, in the presence of a standard, and in the presence of a blank over time is measured, step 208. The initial rate of oxidation of each of the predetermined detection probes is calculated similarly as discussed above with reference to FIGS. 1-8 and equations (1) through (8) to determine the antioxidant capacity of the sample of the skin care product in each of the plurality of homogeneous emulsion mixtures, step 210. The antioxidant capacity of the skin care product in each of the plurality of homogeneous emulsion mixtures is then summed to provide an anti-aging protection factor (APF) score, step 212. The anti-aging protection score is preferably generated by a combination of the results of the ORAC assay, the HORAC assay, the NORAC assay, the SORAC, and the SOAC assay, e.g., as discussed above with reference to FIGS. 4-8. One exemplary APF score for a sample of a skin care product using the ORAC assay, the HORAC assay, the NORAC assay, the SORAC, and the SOAC assay, in accordance with this invention, is summarized below:

| Skin care product/µmol VE/g | ORAC | HORAC | NORAC | SORAC | SOAC | APF score |
|---|---|---|---|---|---|---|
|  | 2,020 | 464 | 1,776 | 1,529 | 3,101 | 8,890 |

The APF score is not limited to the combination of the ORAC assay, the HORAC assay, the NORAC assay, the SORAC, and the SOAC, as any combination of these assays, as well as other assays known by those skilled in the art may be utilized.

The result is the method for assaying an anti-aging protection factor for a skin care product of this invention provides a complete panel assays to test the antioxidant capacity of a skin care product to the predominant ROS/NOS present in the environment and provides an anti-aging protection (APF) score of the skin care product.

EXAMPLES

The following examples are chosen to illustrate and not limit the present invention.

Example 1

ORAC (Antioxidant Capacity against Peroxyl Radicals)

α-Tocopherol, and Tween 20 were purchased from Sigma (St. Louis, Mo.). Linoleic acid methyl ester (methyl linoleate) was obtained from TCI America (Portland, Oreg.). Dihydrorhodamine 6G (DHR-6G) was purchased from Molecular Probes (Eugene, Oreg.). 2,2'-Azobis(2-amidino-propane)dihydrochloride (AAPH) was obtained from Wako Chemicals USA (Richmond, Va.). Various analyzed samples were also obtained. A homogenizer, Model TH-115 with Omni Tip disposable rotor-stator generator probes (Omni International, Marietta, Ga.) was used to emulsify reagents and samples. A Synergy 2 microplate fluorescence reader (Bio-Tek Instruments, Inc., Winooski, Vt.) was used with fluorescence filters for an excitation wavelength of 485±20 nm and an emission wavelength of 528±20 nm. The plate reader was controlled by software Gen 5 (version 1.04) (Bio-Tek Instruments, Inc.). Sample dilution was accomplished by a Precision 2000 automatic pipetting system managed by precision power software (version 1.0) (Bio-Tek Instruments, Inc.).

Reagents and Standards Preparation. Emulsion blank was prepared from 20 mL of deionized water, 2 mL of decane, and 10 drops of Tween 20 by emulsifying emulsified using a homogenizer. This blank was used to dissolve emulsion samples as well as for dilution liquid. 2 mL of methyl linoleate and 10 drops of Tween 20 were added into 20 mL of 21-µM DHR-6G, and emulsified using a homogenizer. Vitamin E standard solution was prepared by emulsifying 2 mL of deionized water, 0.2 mL of 3700 µM Vitamin E solution, and 1 drop of Tween 20.

Sample preparation. Pure compounds were directly dissolve in decane, and mixed with water and Tween 20 to prepare testing solution in emulsion condition. Liquid samples (mostly oil form) were diluted by decane. 0.2 mL of diluted sample was then mixed with 2 mL of water and 1 drop of Tween 20. 0.2 grams of cream samples were accurately weighed and dissolved in 2 mL for emulsion blank.

Figure 10:
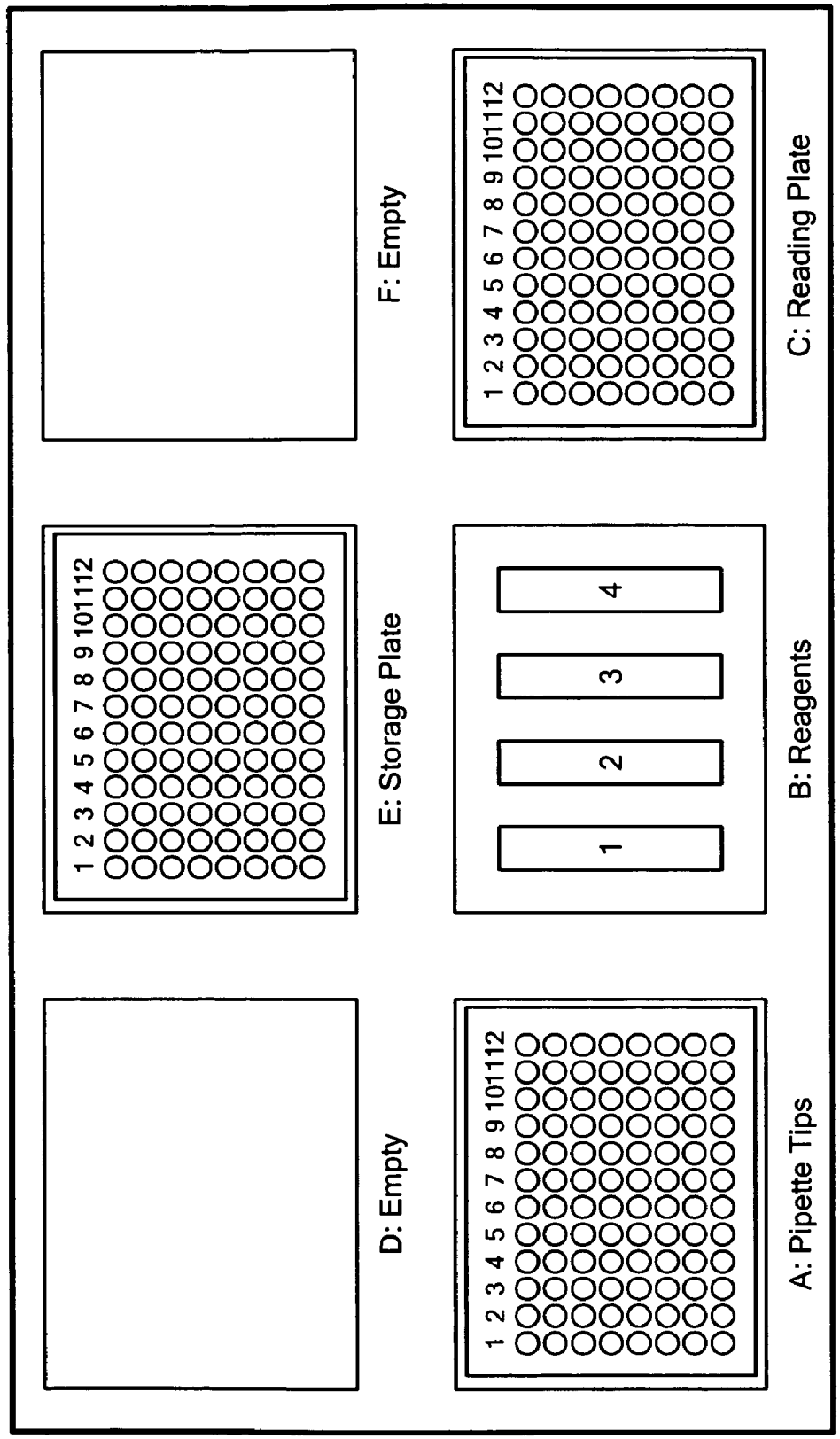
FIG. 10 is a schematic diagram showing one example of the layout of the deck of a Bio-Tek Precision 2000 used in the Example Section of this invention.

Automated Sample Preparation. The automated sample preparation was performed using a Precision 2000. The layout of the deck of the Bio-Tek Precision 2000 is shown in FIG. 10. Details of the operation of a Precision 2000 are disclosed in U.S. Pat. No. 7,132,296, cited supra. As shown, a 250 µL pipette rack was placed at stations A. Station B was the reagent vessel in which 20 mL of emulsion blank was added in reagent holder 1 and 20 mL of DHR-6G working solution was placed in reagent holder 2. A 96-well storage plate (maximum well volume=320 µL) was placed at station E for sample dilution and in station C a reading plate was placed for the final solution. In the storage plate, 200 µL reagents were added manually into #1 and #12 wells. Briefly, 200 µL of emulsion blank was pipetted into wells H1, and H12. 200 µL of Vitamin E standard solution was added to wells B1, B12, D1 and D12. Then ten 200-µL different samples were dispensed into wells A1, A12, C1, C12, E1, E12, F1, F12, G1 and G12. The sample dilution sequence was programmed and controlled by the precision power software (version 1.10). Consecutive 1:2 dilutions were performed and this would give a series of 1:2, 1:4, 1:8, 1:16 and 1:32 dilutions. Care was taken to ensure homogeneity of each dilution by thorough mixing at each stage through repeated aspiration and dispensing programmed by the precision power software.

A full automation of plate-to-plate liquid transfer was programmed. 150 µL of DHR-6G working solution was pipetted into each well at station C. Then 25 µL of diluted sample solution from each well of storage plate was transferred into corresponding reading plate well. FIG. 11 illustrates the layout of the reading plate. The reading plate was covered with a lid and incubated for 20 min in a 37° C. oven. 10 mL of 0.0828 g/mL AAPH solution was placed in reagent holder 4 at station B right after the incubation. The reading plate was then placed back to station C followed by the addition of 25 µL of AAPH solution. The reading plate was immediately placed into plate reader, and kinetic readings were taken every minute for 10 min. Table 2 below shows the Relative ORAC Values of Representative Cream Samples with Antioxidant Activities where the ORAC values are expressed as μmole α-tocopherol (VtE) equivalent per gram. See Table 2 below.

TABLE 2

Relative ORAC Values of Representative Cream Samples with Antioxidant Activities where the ORAC values are expressed as μmole α-tocopherol (VtE) equivalent per gram.

| Sample | ORAC (μmol VE/g) |
|---|---|
| Cream 1 | 1,470 |
| Cream 2 | 20 |
| Cream 3 | 40 |
| Cream 4 | 80 |
| Cream 5 | 4,080 |
| Cream 6 | 1,110 |
| Cream 7 | 1,660 |

Example 2

HORAC (Antioxidant Capacity against Hydroxyl Radicals)

Cobalt (II) fluoride tetrahydrate, fluorescein sodium, picolinic acid, α-tocopherol, and Tween 20 were purchased from Sigma (St. Louis, Mo.). Methyl linoleate was obtained from TCI America (Portland, Oreg.). Dihydrorhodamine 6G (DHR-6G) was obtained from Molecular Probes (Eugene, Oreg.). Hydrogen peroxide, 30% solution was purchased from VWR International (West Chester, Pa.). Various analyzed samples were also obtained. A homogenizer, Model TH-115 with Omni Tip disposable rotor-stator generator probes (Omni International, Marietta, Ga.) was used to emulsify reagents and samples. A Synergy 2 microplate fluorescence reader (Bio-Tek Instruments, Inc., Winooski, Vt.) was used with fluorescence filters for an excitation wavelength of 485±20 nm and an emission wavelength of 528±20 nm. The plate reader was controlled by software Gen 5 (version 1.04) (Bio-Tek Instruments, Inc.). Sample dilution was accomplished by a Precision 2000 automatic pipetting system managed by precision power software (version 1.0) (Bio-Tek Instruments, Inc.).

Reagents and Standards Preparation. Emulsion blank was prepared from 20 mL of phosphate buffer (pH 7.5), 2 mL of decane, and 10 drops of Tween 20 by emulsifying using a homogenizer. This blank was used to dissolve emulsion samples as well as for dilution. 2 mL of methyl linoleate and 10 drops of Tween 20 were added into 20 mL of 2.81 mM DHR-6G, and emulsified using a homogenizer to prepare 2.1 μM DHR-6G working solution in emulsion condition. 0.015 g of cobalt fluoride and 0.0219 g picolinic acid were dissolved in 40 mL of 75 mM phosphate buffer (pH 7.4) to give cobalt fluoride/picolinic acid working solution. Hydrogen peroxide solution was prepared by mixing 12.5 mL of 30% hydrogen peroxide and 7.5 mL of deionized water. Vitamin E standard solution was prepared by emulsifying 2 mL of deionized water, 0.2 mL of 18.60 mM Vitamin E solution, and 1 drop of Tween 20.

Sample preparation. Pure compounds were directly dissolve in decane, and mixed with water and Tween 20 to prepare testing solution in emulsion condition. Liquid samples (mostly oil form) were diluted by decane. 0.2 mL of diluted sample was then mixed with 2 mL of water and 1 drop of Tween 20. 0.2 grams of cream samples were accurately weighed and dissolved in 2 mL for emulsion blank.

Automated Sample Preparation. The automated sample preparation was performed using a Precision 2000. The layout of the deck of the Bio-Tek Precision 2000 is illustrated in FIG. 10. As shown, a 250 μL pipette rack was placed at stations A. Station B was the reagent vessel in which 20 mL of emulsion blank was added in reagent holder 1 and 20 mL of DHR-6G in emulsion condition was placed in reagent holder 2. A 96-well storage plate (maximum well volume=320 μL) was placed at station E for sample dilution and in station C a reading plate was placed for the final solution. In the storage plate, 200 μL reagents were added manually into #1 and #12 wells. Briefly, 200 μL of emulsion blank was pipetted into wells A1, H1, A12, and H12. 200 μL of Vitamin E standard solution was added to wells B1 and B12, C1, C12. Then ten 200-μL different samples were dispensed into wells A1, A12, D1, D12, E1, E12, F1, F12, G1 and G12. The sample dilution sequence was programmed and controlled by the precision power software (version 1.10). Consecutive 1:2 dilutions were performed and this would give a series of 1:2, 1:4, 1:8, 1:16 and 1:32 dilutions. Care was taken to ensure homogeneity of each dilution by thorough mixing at each stage through repeated aspiration and dispensing programmed by the precision power software.

A full automation of plate-to-plate liquid transfer was programmed. 150 μL of DHR-6G working solution was pipetted into each well at station C Then 25 μL of diluted sample solution from each well of storage plate was transferred into corresponding reading plate well. FIG. 12 illustrates the layout of the reading plate. The reading plate was covered with a lid and incubated for 20 min in a 37° C. oven. 20 mL of hydrogen peroxide solution was placed in reagent holder 3, and 20 mL of cobalt fluoride/picolinic acid working solution was placed in reagent holder 4 at station B right after the incubation. The reading plate was then placed back to station C followed by the addition of 12 μL of hydrogen peroxide solution, and 13 μL of cobalt fluoride/picolinic acid solution. The reading plate was immediately placed into plate reader, and kinetic readings were taken every minute for 60 min. Table 3 below shows the Relative HORAC Values of Representative Cream Samples with Antioxidant Activities where the HORAC values are expressed as μmole α-tocopherol (VtE) equivalent per gram. See Table 3 below.

TABLE 3

Relative HORAC Values of Representative Cream Samples with Antioxidant Activities where the HORAC values are expressed as μmole α-tocopherol (VtE) equivalent per gram.

| Sample | HORAC (μmol VE/g) |
|---|---|
| Cream 1 | 24,840 |
| Cream 2 | 21,690 |
| Cream 3 | 19,140 |
| Cream 4 | 23,680 |
| Cream 5 | 112,240 |
| Cream 6 | 41,570 |
| Cream 7 | 20,760 |

Example 3

NORAC (Antioxidant Capacity against Peroxynitrite)

Dihydrorhodamine-123 (DHR-123), sodium hydrogencarbonate, α-tocopherol, and Tween 20 were purchased from Sigma (St. Louis, Mo.). Methyl linoleate was obtained from TCI America (Portland, Oreg.). 3-morpholinosydnonimine, hydrochloride (SIN-1) was purchased from Toronto Research Chemicals (North York, On, Canada). Various analyzed samples were also obtained. A homogenizer, Model TH-115 with Omni Tip disposable rotor-stator generator probes (Omni International, Marietta, Ga.) was used to emulsify reagents and samples. A Synergy 2 microplate fluorescence reader (Bio-Tek Instruments, Inc., Winooski, Vt.) was used with fluorescence filters for an excitation wavelength of 485±20 nm and an emission wavelength of 528±20 nm. The plate reader was controlled by software Gen 5 (version 1.04) (Bio-Tek Instruments, Inc.). Sample dilution was accomplished by a Precision 2000 automatic pipetting system managed by precision power software (version 1.0) (Bio-Tek Instruments, Inc.).

Reagents and Standards Preparation. Emulsion blank was prepared from 20 mL of hydrogencarbonate/phosphate buffer, 2 mL of decane, and 10 drops of Tween 20 by emulsifying emulsified using a homogenizer. This blank was used to dissolve emulsion samples as well as for dilution liquid. 2.75 mL of methyl linoleate and 15 drops of Tween 20 were added into 27.6 mL of 1.0-µM DHR-123, and emulsified using a homogenizer. 0.004 g of SIN-1 was dissolved in hydrogencarbonate/phosphate buffer to give SIN-1 solution. Vitamin E standard solution was prepared by emulsifying 2 mL of deionized water, 0.2 mL of 1850-µM Vitamin E solution, and 1 drop of Tween 20.

Sample preparation. Pure compounds were directly dissolve in decane, and mixed with water and Tween 20 to prepare testing solution in emulsion condition. Liquid samples (mostly oil form) were diluted by decane. 0.2 mL of diluted sample was then mixed with 2 mL of water and 1 drop of Tween 20. 0.2 grams of cream samples were accurately weighed and dissolved in 2 mL for emulsion blank.

Automated Sample Preparation. The automated sample preparation was performed using a Precision 2000. The layout of the deck of the Bio-Tek Precision 2000 is illustrated in FIG. 10. As shown, a 250 µL pipette rack was placed at stations A. Station B was the reagent vessel in which 20 mL of blank emulsion was added in reagent holder 1 and 30 mL of DHR-123 working solution in emulsion condition was placed in reagent holder 2. A 96-well storage plate (maximum well volume=320 µL) was placed at station E for sample dilution and in station C a reading plate was placed for the final solution. In the storage plate, 200 µL reagents were added manually into #1 and #12 wells. Briefly, 200 µL of emulsion blank was pipetted into wells H1, and H12. 200 µL of Vitamin E standard solution was added to wells B1, B12, D1 and D12. Then ten 200-µL different samples were dispensed into wells A1, A12, C1, C12, E1, E12, F1, F12, G1 and G12. The sample dilution sequence was programmed and controlled by the precision power software (version 1.10). Consecutive 1:2 dilutions were performed and this would give a series of 1:2, 1:4, 1:8, 1:16 and 1:32 dilutions. Care was taken to ensure homogeneity of each dilution by thorough mixing at each stage through repeated aspiration and dispensing programmed by the precision power software.

A full automation of plate-to-plate liquid transfer was programmed. 150 µL of DHR-123 working solution was pipetted into each well at station C. Then 25 µL of diluted sample solution from each well of storage plate was transferred into corresponding reading plate well. FIG. 13 illustrates the layout of the reading plate. The reading plate was covered with a lid and incubated for 20 min in a 37° C. oven. Right before the end of incubation, 200 µL of SIN-1 solution was added into row 11 & 12 of an empty microplate and place the plate on rack E. The reading plate was then placed back to station C followed by the addition of 25 µL of SIN-1 solution. The reading plate was immediately placed into plate reader, and kinetic readings were taken every minute for 10 min. Table 4 below shows the Relative NORAC Values of Representative Cream Samples with Antioxidant Activities where the NORAC values are expressed as µmole α-tocopherol (VtE) equivalent per gram. See Table 4 below.

TABLE 4

Relative NORAC Values of Representative Cream Samples with Antioxidant Activities where the NORAC values are expressed as µmole α-tocopherol (VtE) equivalent per gram.

| Sample | NORAC (µmol VE/g) |
| --- | --- |
| Cream 1 | 1,510 |
| Cream 2 | 150 |
| Cream 3 | 270 |
| Cream 4 | 360 |
| Cream 5 | 20,550 |
| Cream 6 | 1,250 |
| Cream 7 | 280 |

Example 4

SORAC (Antioxidant Capacity against Superoxide Anion)

Diethylenetriamine pentaacetic acid (DTPA), manganese (III) 5,10,15,20-tetra(4-pyridyl)-21H,23H-porphine chloride tetrakis(methochloride), superoxide dismutase (SOD), Tween 20, xanthine, and xanthine oxidase suspension were purchased from Sigma (St. Louis, Mo.). Methyl linoleate was obtained from TCI America (Portland, Oreg.). Hydroethidine fluorescent stain was purchased from Polysciences, Inc. (Warrington, Pa.). Sodium hydroxide, pellets was purchased from VWR International (West Chester, Pa.). Various analyzed samples were also obtained. A homogenizer, Model TH-115 with Omni Tip disposable rotor-stator generator probes (Omni International, Marietta, Ga.) was used to emulsify reagents and samples. A Synergy 2 microplate fluorescence reader (Bio-Tek Instruments, Inc., Winooski, Vt.) was used with fluorescence filters for an excitation wavelength of 485±20 nm and an emission wavelength of 590±20 nm. The plate reader was controlled by software Gen 5 (version 1.04) (Bio-Tek Instruments, Inc.). Sample dilution was accomplished by a Precision 2000 automatic pipetting system managed by precision power software (version 1.0) (Bio-Tek Instruments, Inc.).

Reagents and Standards Preparation. Emulsion blank was prepared from 30 mL of DTPA/phosphate buffer, 3 mL of decane, and 15 drops of Tween 20 by emulsifying using a homogenizer. This blank was used to dissolve emulsion samples as well as for dilution liquid. 2 mL of methyl linoleate and 10 drops of Tween 20 were added into 20 mL of 10 µg/mL hydroethidine fluorescent stain stock solution in emulsion condition, and emulsified using a homogenizer. 0.015 g of xanthine was dissolved in 5 mL of 0.1 N sodium hydroxide and 95 mL of DTPA/phosphate buffer to give xanthine working solution. Mn working solution in emulsion condition was prepared by mixing 1144 µM manganese(III) 5,10,15,20-tetra(4-pyridyl)-21H,23H-porphine chloride tetrakis(methochloride) solution into 10 mL of blank emulsion. Xanthine oxidase solution was prepared in DTPA/phosphate buffer. SOD standard solution in emulsion condition was prepared by mixing 0.2 mL of 300-unit SOD stock solution and 1.8 mL of blank emulsion.

Sample preparation. Pure compounds were directly dissolve in decane, and mixed with water and Tween 20 to prepare testing solution in emulsion condition. Liquid samples (mostly oil form) were diluted by decane. 0.2 mL of diluted sample was then mixed with 2 mL of water and 1 drop of Tween 20. 0.2 grams of cream samples were accurately weighed and dissolved in 2 mL for emulsion blank.

Automated Sample Preparation. The automated sample preparation was performed using a Precision 2000. The layout of the deck of the Bio-Tek Precision 2000 is illustrated in FIG. 10. As shown, a 250 µL pipette rack was placed at stations A. Station B was the reagent vessel in which 20 mL of emulsion blank was added in reagent holder 1 and 20 mL of hydroethidine fluorescent stain working solution was placed in reagent holder 2. A 96-well storage plate (maximum well volume=320 µL) was placed at station E for sample dilution and in station C a reading plate was placed for the final solution. In the storage plate, 200 µL reagents were added manually into #1 and #12 wells. Briefly, 200 µL of emulsion blank was pipetted into wells H1, and H12. 200 µL of SOD standard solution was added to wells B1, B12, D1 and D12. Then ten 200-µL different samples were dispensed into wells A1, A12, C1, C12, E1, E12, F1, F12, G1 and G12. The sample dilution sequence was programmed and controlled by the precision power software (version 1.10). Consecutive 1:2 dilutions were performed and this would give a series of 1:2, 1:4, 1:8, 1:16 and 1:32 dilutions. Care was taken to ensure homogeneity of each dilution by thorough mixing at each stage through repeated aspiration and dispensing programmed by the precision power software.

A full automation of plate-to-plate liquid transfer was programmed. 150 µL of hydroethidine fluorescent stain working solution was pipetted into each well at station C. Then 25 µL of diluted sample solution from each well of storage plate was transferred into corresponding reading plate well. FIG. 14 illustrates the layout of the reading plate. The reading plate was covered with a lid and incubated for 20 min in a 37° C. oven. Right before the end of incubation, 200 µL of xanthine oxidase working solution was added into row 11 & 12 of an empty microplate and place the plate on rack E. The reading plate was then placed back to station C followed by the addition of 25 µL of xanthine oxidase working solution. The reading plate was immediately placed into plate reader, and kinetic readings were taken every minute for 10 min. See Table 5 below.

TABLE 5

Relative SORAC Values of Representative Cream Samples with Antioxidant Activities where the SORAC values are expressed as relative superoxide dismutase (SOD) equivalent.

| Sample | SORAC (kunitSODeq/g) |
| --- | --- |
| Cream 1 | 0 |
| Cream 2 | 0 |
| Cream 3 | 0 |
| Cream 4 | 0 |
| Cream 5 | 0.326 |
| Cream 6 | 0.141 |
| Cream 7 | 0 |

Example 5

SOAC (Antioxidant Capacity against Singlet Oxygen)

Lithium molybate, α-tocopherol, and Tween 20 were purchased from Sigma (St. Louis, Mo.). Methyl linoleate was obtained from TCI America (Portland, Oreg.). Hydroethidine fluorescent stain was purchased from Polysciences, Inc. (Warrington, Pa.). Sodium hydroxide, pellets and hydrogen peroxide, 30% solution were purchased from VWR International (West Chester, Pa.). Various analyzed samples were also obtained. A homogenizer, Model TH-115 with Omni Tip disposable rotor-stator generator probes (Omni International, Marietta, Ga.) was used to emulsify reagents and samples. A Synergy 2 microplate fluorescence reader (Bio-Tek Instruments, Inc., Winooski, Vt.) was used with fluorescence filters for an excitation wavelength of 485±20 nm and an emission wavelength of 590±20 nm. The plate reader was controlled by software Gen 5 (version 1.04) (Bio-Tek Instruments, Inc.). Sample dilution was accomplished by a Precision 2000 automatic pipetting system managed by precision power software (version 1.0) (Bio-Tek Instruments, Inc.).

Reagents and Standards Preparation. Emulsion blank was prepared from 20 mL of deionized water, 2 mL of decane, and 10 drops of Tween 20 by emulsifying using a homogenizer. This blank was used to dissolve emulsion samples as well as for dilution liquid. 2 mL of methyl linoleate and 10 drops of Tween 20 were added into 20 mL of 14.5 µg/mL hydroethidine fluorescent stain working solution in emulsion condition, and emulsified using a homogenizer. Hydrogen peroxide solution was prepared by mixing 0.1 mL of 30% hydrogen peroxide and 19.9 mL of deionized water. Vitamin E standard solution was prepared by emulsifying 2 mL of deionized water, 0.2 mL of 18.60 mM Vitamin E solution, and 1 drop of Tween 20. 0.08 g of sodium hydroxide was dissolved in 20 mL of deionized water to give 0.1 N sodium hydroxide solution. Lithium molybate solution was prepared by dissolving 0.032 g of lithium molybate into 20 mL of deionized water.

Sample preparation. Pure compounds were directly dissolve in decane, and mixed with water and Tween 20 to prepare testing solution in emulsion condition. Liquid samples (mostly oil form) were diluted by decane. 0.2 mL of diluted sample was then mixed with 2 mL of water and 1 drop of Tween 20. 0.2 grams of cream samples were accurately weighed and dissolved in 2 mL for emulsion blank.

Automated Sample Preparation. The automated sample preparation was performed using a Precision 2000. The layout of the deck of the Bio-Tek Precision 2000 is illustrated in FIG. 10. As shown, a 250 µL pipette rack was placed at stations A. Station B was the reagent vessel in which 20 mL of emulsion blank was added in reagent holder 1 and 20 mL of hydroethidine fluorescent stain working solution was placed in reagent holder 2. A 96-well storage plate (maximum well volume=320 µL) was placed at station E for sample dilution and in station C a reading plate was placed for the final solution. In the storage plate, 200 µL reagents were added manually into #1 and #12 wells. Briefly, 200 µL of emulsion blank was pipetted into wells H1, and H12. 200 µL of Vitamin E standard solution was added to wells B1, B12, D1 and D12. Then ten 200-µL different samples were dispensed into wells A1, A12, C1, C12, E1, E12, F1, F12, G1 and G12. The sample dilution sequence was programmed and controlled by the precision power software (version 1.10). Consecutive 1:2 dilutions were performed and this would give a series of 1:2, 1:4, 1:8, 1:16 and 1:32 dilutions. Care was taken to ensure homogeneity of each dilution by thorough mixing at each stage through repeated aspiration and dispensing programmed by the precision power software.

A full automation of plate-to-plate liquid transfer was programmed. 150 µL of hydroethidine fluorescent stain working solution was pipetted into each well at station C. Then 25 µL of diluted sample solution from each well of storage plate was transferred into corresponding reading plate well. FIG. 15 illustrates the layout of the reading plate. The reading plate was covered with a lid and incubated for 20 min in a 37° C. oven. 20 mL of lithium molybate solution was placed in reagent holder 2, 20 mL of hydrogen peroxide solution was placed in reagent holder 3, and 20 mL of sodium hydroxide solution was placed in reagent holder 4 at station B right after the incubation. The reading plate was then placed back to station C followed by the addition of 25 µL of lithium molybate solution, 25 µL of hydrogen peroxide solution, and 10 µL of sodium hydroxide solution. The reading plate was immediately placed into plate reader, and kinetic readings were taken every minute for 30 min. Table 6 below shows the Relative SOAC Values of Representative Cream Samples with Antioxidant Activities SOAC values are expressed as µmole α-tocopherol (VtE) equivalent per gram. See Table 6 below.

TABLE 6

Relative SOAC Values of Representative Cream Samples with Antioxidant Activities SOAC values are expressed as µmole α-tocopherol (VtE) equivalent per gram.

| Sample | SOAC (µmole VE/g) |
| --- | --- |
| Cream 1 | 2,330 |
| Cream 2 | 1,460 |
| Cream 3 | 1,380 |
| Cream 4 | 1,710 |
| Cream 5 | 16,240 |
| Cream 6 | 1,460 |
| Cream 7 | 1,850 |

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A method for assaying the antioxidant capacity of a skin care product, the method comprising:
    preparing an emulsion base configured to not alter or destroy the formulation of a sample of the skin care product;
    dissolving a sample of the skin care product into the emulsion base to form a homogeneous emulsion mixture;
    adding an emulsion detection probe to the homogeneous emulsion mixture;
    adding reactive oxygen species generator and/or a reactive nitrogen species generator to the homogeneous emulsion mixture;
    measuring the fluorescence intensity change of the detection probe in the presence of the sample over time, in the presence of a standard over time, and in the presence of a blank over time; and
    calculating the initial rate of oxidation of the detection probe to determine the antioxidant capacity of the sample of the skin care product.

2. The method of claim 1 in which the detection probe is a non-protein probe.

3. The method of claim 2 in which the non-protein probe includes a hydrogen atom donor probe.

4. The method of claim 3 in which the detection probe is chosen from the group consisting of dihydrorhodamine-6G,2, methyl 2-(3,6-diamino-9H-xanthene-9-yl)benzoate (dihydrorhodamine-123), and 5-ethyl-5,6-dihydro-6-phenyl-3,8-phenanthridinediamine (hydroethidine).

5. The method of claim 1 in which the detection probe is chosen for a predetermined reactive oxygen species and/or a predetermined reactive nitrogen species.

6. The method of claim 5 in which the detection probe includes dihydrorhodamine-6G and the reactive oxygen species including peroxyl radicals.

7. The method of claim 5 in which the detection probe includes 2-(6-hydroxy-3-oxo-xanthen-9-yl)benzoic acid and the hydroxyl reactive oxygen species includes hydroxyl radicals.

8. The method of claim 5 in which a the detection probe includes methyl 2-(3,6-diamino-9H-xanthene-9-yl)benzoate and the reactive nitrogen species includes peroxynitrites.

9. The method of claim 5 in which the detection probe includes 5-ethyl-5,6-dihydro-6-phenyl-3,8-phenanthridinediamine and the reactive oxygen species includes superoxide anions.

10. The method of claim 5 in which the detection probe includes 5-ethyl-5,6-dihydro-6-phenyl-3,8-phenanthridinediamine and the reactive oxygen species includes singlet oxygen.

11. The method of claim 5 in which the reactive oxygen species generator and/or the reactive nitrogen species is chosen to generate the predetermined reactive oxygen species and/or the predetermined reactive nitrogen species.

12. The method of claim 11 in which the reactive oxygen species generator includes 2,2-Azobis (2-amidino-propane) dihydrochloride (AAPH) and the reactive oxygen species includes peroxyl radicals.

13. The method of claim 11 in which the reactive oxygen species generator includes a combination of cobalt fluoride, picolinic acid, and hydrogen peroxide and the reactive oxygen species includes hydroxyl radicals.

14. The method of claim 11 in which the reactive nitrogen species generator includes 3-morpholinosyndnonimine hydrochloride and the reactive nitrogen species includes peroxynitrites.

15. The method of claim 11 in which the reactive oxygen species generator includes a combination of xanthin and xanthin oxidase and the reactive oxygen species includes superoxide anions.

16. The method of claim 11 in which the reactive oxygen species generator includes a combination of lithium molybate, sodium hydroxide, and hydrogen peroxide and the reactive oxygen species includes singlet oxygen.

17. The method of claim 1 in which the sample is dissolved in the emulsion base by vortex mixing.

18. The method of claim 1 in which the sample is dissolved in the emulsion base using an emulsifier.

19. The method of claim 18 in which the standard includes 2,5,7,8-Tetramethyl-2-(4',8',12'-trimethyltridecyl)-6-chromanol (Vitamin E).

20. The method of claim 18 in which the standard includes a mixture of the detection probe, the chemical having a known antioxidant capacity, and the emulsion base.

21. The method of claim 1 in which the emulsion base is comprised of an oil, water, and a surfactant.

22. The method of claim 1 in which the standard has a known antioxidant capacity.

23. The method of claim 1 in which the blank includes a mixture of the detection probe and the emulsion base.

24. The method of claim 1 in which assaying the antioxidant capacity of a sample includes an assay chosen from the group consisting of: an Oxygen Radical Absorbance Capacity (ORAC) assay, a Hydroxy Radical Averting Capacity (HORAC) assay, a No Radical Absorbance Capacity (NORAC) assay, a Super Oxide Radical Absorbance Capacity (SORAC), and a Singlet Oxygen Absorbance Capacity (SOAC).

25. A method for assaying an anti-aging protection factor for a skin care product, the method comprising:
preparing a plurality of emulsions bases each configured to not alter or destroy the formulation of a sample of the skin care product;
dissolving a sample of the skin care product into each of said plurality of emulsion bases to form a plurality of homogeneous emulsion mixtures;
adding a predetermined emulsion detection probe specific for a predetermined reactive oxygen species and/or a predetermined reactive nitrogen species to each of said plurality homogeneous emulsion mixtures;
adding reactive oxygen species generator and/or a reactive nitrogen species specific for each of the predetermined reactive oxygen species and/or the predetermined nitrogen species to each of the plurality of homogeneous emulsion mixtures;
measuring the fluorescence intensity change of each of said predetermined detection probes in the presence of each said sample in the presence of a standard, and in the presence of a blank over time; and
calculating the initial rate of oxidation of each of said predetermined detection probes to determine the antioxidant capacity of the sample of the skin care product in each of the plurality of homogeneous emulsion mixtures and provide an anti-aging protection factor score.

26. The method of claim 25 in which the antioxidant capacity of the skin care product in each of the plurality of homogeneous emulsion mixtures is summed to provide an anti-aging protection factor score.

27. The method of claim 26 in which the anti-aging protection score is generated by a combination of one or more of: an Oxygen Radical Absorbance Capacity (ORAC) assay, a Hydroxy Radical Averting Capacity (HORAC) assay, a No Radical Absorbance Capacity (NORAC) assay, a Super Oxide Radical Absorbance Capacity (SORAC), and a Singlet Oxygen Absorbance Capacity (SOAC).

28. The method of claim 25 in which the detection probe is a non-protein probe.

29. The method of claim 28 in which the non-protein probe includes a hydrogen atom donor probe.

30. The method of claim 25 in which the detection probe is chosen from the group consisting of dihydrorhodamine-6G, Methyl 2-(3,6-diamino-9H-xanthene-9-yl)benzoate (dihydrorhodamine-123), and 5-ethyl-5,6-dihydro-6-phenyl-3,8-phenanthridinediamine (hydroethidine).

31. The method of claim 25 in which the detection probe is chosen for a predetermined reactive oxygen species and/or a predetermined reactive nitrogen species.

32. The method of claim 31 in which the detection probe includes dihydrorhodamine-6G and the reactive oxygen species includes peroxyl radicals.

33. The method of claim 31 in which the detection probe includes dihydrorhodamine-6G and the hydroxyl reactive oxygen species includes hydroxyl radicals.

34. The method of claim 31 in which a the detection probe includes methyl 2-(3,6-diamino-9H-xanthene-9-yl)benzoate and the reactive nitrogen species includes peroxynitrites.

35. The method of claim 31 in which the detection probe includes 5-ethyl-5,6-dihydro-6-phenyl-3,8-phenanthridinediamine and the reactive oxygen species includes superoxide anions.

36. The method of claim 31 in which the detection probe includes 5-ethyl-5,6-dihydro-6-phenyl-3,8-phenanthridinediamine and the reactive oxygen species includes singlet oxygen.

37. The method of claim 31 in which the reactive oxygen species generator and/or the reactive nitrogen species is chosen to generate the predetermined reactive oxygen species and/or the predetermined reactive nitrogen species.

38. The method of claim 37 in which the reactive oxygen species generator includes 2,2-Azobis (2-amidino-propane) dihydrochloride (AAPH) and the reactive oxygen species includes peroxyl radicals.

39. The method of claim 37 in which the reactive oxygen species generator includes a combination of cobalt fluoride, picolinic acid and hydrogen peroxide and the reactive oxygen species includes hydroxyl radicals.

40. The method of claim 37 in which the reactive nitrogen species generator includes 3-morpholinosyndnonimine hydrochloride and the reactive nitrogen species includes peroxynitrites.

41. The method of claim 37 in which the reactive oxygen species generator includes a combination of xanthin and xanthin oxidase and the reactive oxygen species includes superoxide anions.

42. The method of claim 37 in which the reactive oxygen species generator includes a combination of: lithium molybate, sodium hydroxide, and hydrogen peroxide and the reactive oxygen species includes singlet oxygen.

43. The method of claim 25 in which the sample is dissolved in each of said emulsion bases by vortex mixing.

44. The method of claim 25 in which the sample is dissolved in each of said emulsion bases using an emulsifier.

45. The method of claim 25 in which each of the plurality of emulsion bases is comprised of oil, water, and a surfactant.

46. The method of claim 25 in which the standard has a known antioxidant capacity.

47. The method of claim 46 in which the standard includes 2,5,7,8-Tetramethyl-2-(4',8',12'-trimethyltridecyl)-6-chromanol (Vitamin E).

48. The method of claim 25 in which the standard includes a mixture of the detection probe, a chemical having a known antioxidant capacity, and the emulsion base.

49. The method of claim 25 in which the blank includes a mixture of the detection probe and the emulsion base.

* * * * *